(12) United States Patent
Tang et al.

(10) Patent No.: US 11,319,328 B2
(45) Date of Patent: May 3, 2022

(54) 4β-AMINO SUBSTITUTED PODOPHYLLOTOXIN DERIVATIVE AND PREPARATION METHOD THEREFOR AND USE THEREOF

(71) Applicant: Yajie Tang, Hubei (CN)

(72) Inventors: Yajie Tang, Hubei (CN); Wei Zhao, Hubei (CN)

(73) Assignee: Yajie Tang

( * ) Notice: Subject to any disclaimer, the term of this patent is extended or adjusted under 35 U.S.C. 154(b) by 0 days.

(21) Appl. No.: 16/639,029

(22) PCT Filed: Jun. 4, 2018

(86) PCT No.: PCT/CN2018/089831
§ 371 (c)(1),
(2) Date: Feb. 13, 2020

(87) PCT Pub. No.: WO2019/033829
PCT Pub. Date: Feb. 21, 2019

(65) Prior Publication Data
US 2020/0223862 A1 Jul. 16, 2020

(30) Foreign Application Priority Data
Aug. 16, 2017 (CN) .......................... 201710755830.9

(51) Int. Cl.
*C07D 493/04* (2006.01)
*A61P 35/00* (2006.01)
(52) U.S. Cl.
CPC ............ *C07D 493/04* (2013.01); *A61P 35/00* (2018.01)
(58) Field of Classification Search
CPC ................................................... C07D 493/04
See application file for complete search history.

(56) References Cited

U.S. PATENT DOCUMENTS 6,903,133 B2 * 6/2005 Shi .......................... A61P 35/04
514/463
2008/0275248 A1 11/2008 Ahmed et al.
2019/0029997 A1 1/2019 Zhang et al.

FOREIGN PATENT DOCUMENTS

| CN | 101074233 A | 11/2007 |
| CN | 102875564 A | 1/2013 |
| CN | 105732651 A | 7/2016 |
| WO | 2004033423 A2 | 4/2004 |
| WO | 2004073375 A2 | 9/2004 |

OTHER PUBLICATIONS

Hu et al., Mol. Biosyst., 2010, 6, pp. 410-420.*
International Search Report for Application No. PCT/CN2018/089831, dated Jul. 31, 2018, pp. 1-3.

* cited by examiner

*Primary Examiner* — Alicia L Otton
(74) *Attorney, Agent, or Firm* — Lerner, David, Littenberg, Krumholz & Mentlik, LLP

(57) ABSTRACT

Disclosed are a 4β-amino substituted podophyllotoxin derivative and a synthesis method therefor and the use thereof. The present invention respectively introduces the aromatic heterocyclic compounds anthraquinone, quinazoline, quinoline, indole, indazole, pyrimidine as substituent groups to position-4 of the C ring in the podophyllotoxin or 4'-demethylepipodophyllotoxin to obtain the podophyllotoxin derivatives as shown in formula (V). Experiments involving in vitro tumour cell activity inhibition show that the antitumour activity of most of the compounds as shown in formula (V) of the present invention is significantly improved compared to that of the patented medicine of podophyllotoxin-"etoposide".

11 Claims, 3 Drawing Sheets

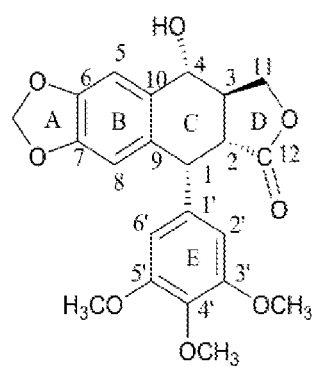
(podophyllotoxin)
formula( I )
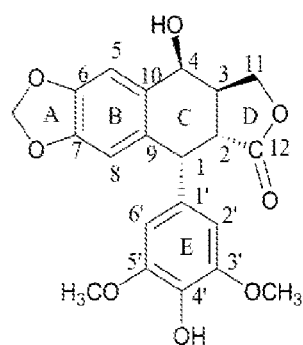
(4'-demethylepipodophyllotoxin)
formula( II )
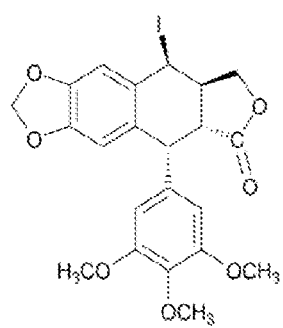
(I-podophyllotoxin)
formula( III )
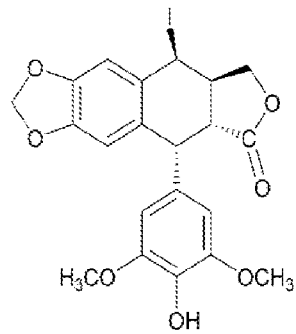
( I-4'-demethylepipodophyllotoxin)
formula(IV)
Fig. 1

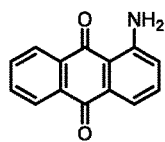
1-amino anthraquinone
(1)

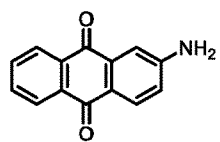
2-amino anthraquinone
(2)

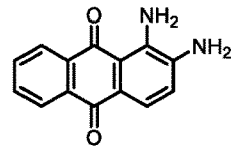
1,2-diaminoanthraquinone
(3)

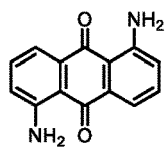
1,5-diamino anthraquinone
(4)

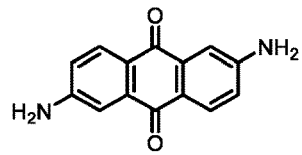
2,6-diamino anthraquinone
(5)

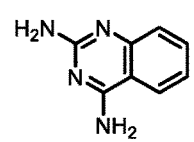
2,4-quinazolinediamine
(6)

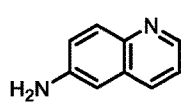
6-aminoquinoline
(7)

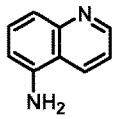
5-aminoquinoline
(8)

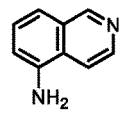
5-aminoisoquinoline
(9)

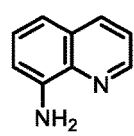
8- aminoquinoline
(10)

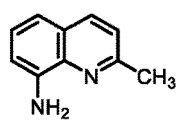
8-aminoquinaldine
(11)

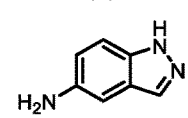
5-indazolamine
(12)

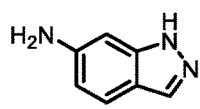
6-indazolamine
(13)

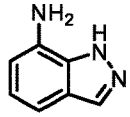
7-indazolamine
(14)

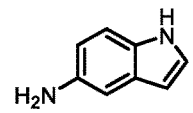
5-aminoindole
(15)

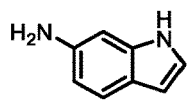
6-aminoindole
(16)

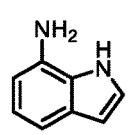
7-aminoindole
(17)

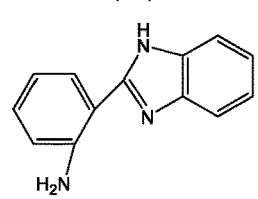
2-(2-aminophenyl)
benzimidazole
(18)

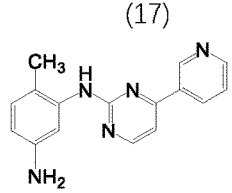
N-(5-amino-2- methylphenyl)-4-(3-pyridyl)-2-pyrimidineamine
(19)

Fig. 2

4β-AMINO SUBSTITUTED PODOPHYLLOTOXIN DERIVATIVE AND PREPARATION METHOD THEREFOR AND USE THEREOF

CROSS REFERENCE TO RELATED APPLICATIONS

The present application is a U.S. national phase entry under 35 U.S.C. § 371 of International Application No. PCT/CN2018/089831, filed Jun. 4, 2018, which claims priority from Chinese Patent Application No. 201710755830.9 filed Aug. 16, 2017, all of which are hereby incorporated herein by reference.

TECHNICAL FIELD

The invention belongs to the field of podophyllotoxin derivatives, in particular to 4β-amino substituted podophyllotoxin derivatives and a preparation method therefor, and the invention also relates to use of the 4β-amino substituted podophyllotoxin derivatives in the preparation of antitumor drugs.

BACKGROUND ART

The structures of podophyllotoxin and 4'-demethylepipodophyllotoxin are shown in formula (I) and (II) in FIG. 1. Podophyllotoxin and 4'-demethylepipodophyllotoxin are natural active lead compounds with broad-spectrum antitumor activity extracted from podophyllotoxin plants (e.g. *Sinopodophyllum hexandrum*, *Dickinsia hydrocotyloides*, *Dysosma versipellis*, etc.). However, the clinical applications are limited due to their strong toxic side effects and poor bioavailability.

SUMMARY OF THE INVENTION

The first object of the present invention is to provide a class of 4β-amino substituted podophyllotoxin derivatives having good antitumor activities;

The second object of the present invention is to provide a method for preparing the 4β-amino substituted podophyllotoxin derivatives;

The third object of the present invention is to apply the 4β-amino substituted podophyllotoxin derivatives to the preparation of clinical antitumor drugs.

The above object of the present invention is achieved by the following technical solution:

a class of 4β-amino substituted podophyllotoxin derivatives with antitumor activity or pharmaceutically acceptable salts thereof, wherein the structural formula of the podophyllotoxin derivatives is shown as (V):

Formula (V)

Wherein $R_1$ is selected from

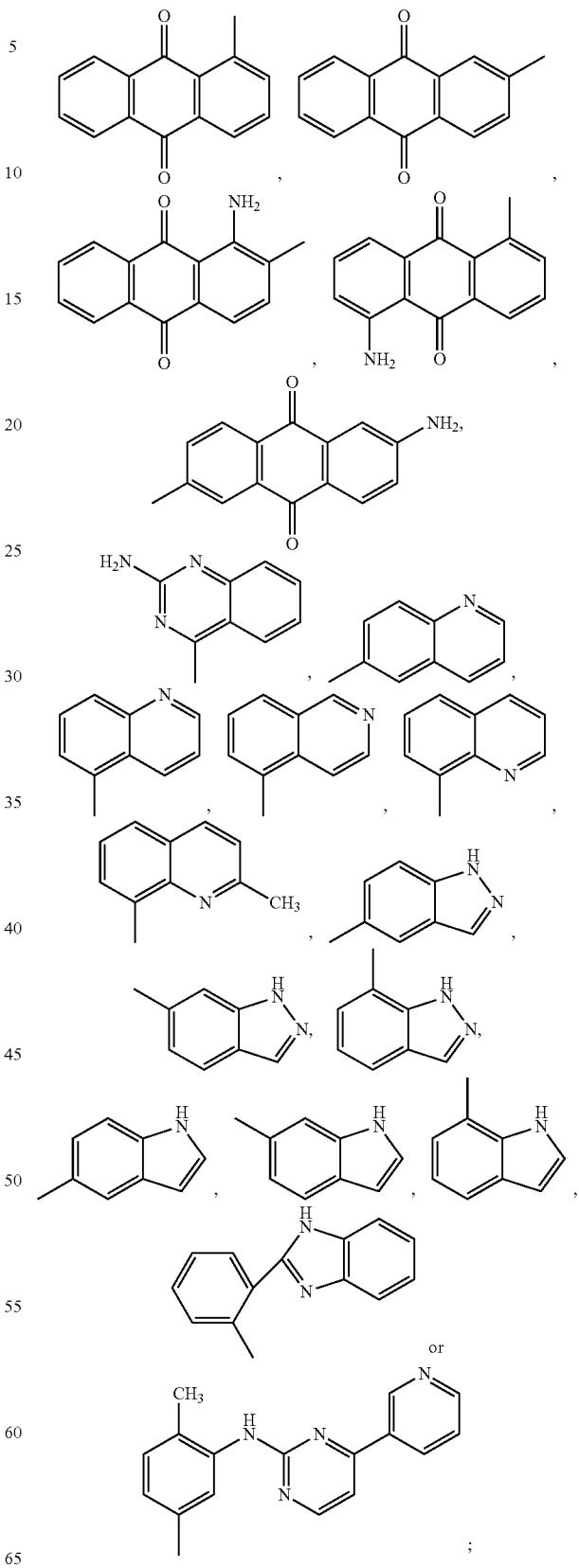

$R_2$ is hydrogen or —$CH_3$.

The invention adopts aromatic heterocyclic compounds including 1-aminoanthraquinone, 2-aminoanthraquinone, 1,2-diaminoanthraquinone, 1,5-diaminoanthraquinone, 2,6-diaminoanthraquinone, 2,4-quinazolinediamine, 6-aminoquinoline, 5-aminoquinoline, 5-aminoisoquinoline, 8-aminoquinoline, 8-aminoquinaldine, 5-indazolamine, 6-indazolamine, 7-indazolamine, 5-aminoindole, 6-aminoindole, 7-aminoindole, 2-(2-aminophenyl) benzimidazole and N-(5-amino-2-methylphenyl)-4-(3-pyridyl)-2-aminopyrimidine, as shown in FIG. 2, which are used as substituent groups to facilitate the formation of the β-configuration of position-4 of the C ring in podophyllotoxin and 4'-demethylepipodophyllotoxin, so that the podophyllotoxin derivatives with further improved antitumor activity and reduced toxic and side effects are obtained.

The method for preparing the compound shown in the formula (V) comprises the steps of:
A, introducing iodine into position-4 of the C ring in podophyllotoxin or 4'-demethylepipodophyllotoxin through an iodine substitution reaction to form iodopodophyllotoxin or iodo4'-demethylepipodophyllotoxin, shown in the formula III and IV in FIG. 1;
B. introducing a reaction monomer into position-4 of the C ring in iodopodophyllotoxin or iodo4'-demethylepipodophyllotoxin through a nucleophilic substitution reaction, wherein the reaction monomer may be selected from the group consisting of 1-amino anthraquinone, 2-amino anthraquinone, 1,2-diamino anthraquinone, 1,5-diamino anthraquinone, 2,6-diamino anthraquinone, 2,4-quinazolinediamine, 6-aminoquinoline, 5-aminoquinoline, 5-aminoisoquinoline, 8-aminoquinoline, 8-aminoquinaldine, 5-indazolamine, 6-indazolamine, 7-indazolamine, 5-aminoindole, 6-aminoindole, 7-aminoindole, 2-(2-aminophenyl) benzimidazole or N-(5-amino-2-methylphenyl)-4-(3-pyridyl)-2-aminopyrimidine.

The iodine substitution reaction is performed as follows: dissolving podophyllotoxin or 4'-demethylepipodophyllotoxin in acetonitrile, adding NaI or KI, then adding a proper amount of boron trichloride diethyl ether for catalysis, followed by stirring for reaction.

Wherein the molar ratio of podophyllotoxin or 4'-demethylepipodophyllotoxin to NaI or KI may be from 1:1-1.5, for example 1:1-1.3, as well as 1:1.

The boron trichloride diethyl ether is added dropwise in an ice bath, followed by stirring for reaction at a certain temperature.

The nucleophilic substitution reaction is performed as follows: dissolving the reaction monomer with iodopodophyllotoxin or iodo4'-demethylepipodophyllotoxin in an organic solvent, adding a catalyst and an acid-binding agent, followed by stirring to obtain the compound. The iodopodophyllotoxin or iodo4'-demethylepipodophyllotoxin is a product obtained by spin-drying after iodine substitution reaction.

Wherein the molar ratio of the reaction monomer to iodopodophyllotoxin or iodo4'-demethylepipodophyllotoxin may be 3:1-1:1, for example 1:1.

In the present invention, the organic solvent may be tetrahydrofuran, acetone, chloroform, ethanol or acetonitrile, the catalyst may be $BaCO_3$, and the acid-binding agent may be triethylamine or pyridine.

Wherein the nucleophilic substitution reaction is firstly reacted in an ice bath, the reaction time may be 0.5-5 h, for example 1-3 h, and then the reaction is performed at a certain temperature, and the reaction time may be 5-72 h, for example 13-15 h.

In the present invention, the certain temperature in the iodine substitution reaction and nucleophilic substitution reaction is 15-40° C., for example 20-30° C.

In the present invention, the stirring rotation speed in the iodine substitution reaction may be 100-600 rpm.

The preparation method further comprises the steps of: filtering the reaction solution after nucleophilic substitution reaction, spin-drying the filtrate, and performing preparation and separation by using silica gel column chromatography or a reverse phase chromatography column to obtain purified 4β-amino substituted podophyllotoxin derivatives products.

Preferably, the separation method using the silica gel column chromatography comprises the steps of: (1) packing and equilibrating the silica gel column chromatography belonging to normal phase silica gel column chromatography with an eluent, wherein the eluent is preferably the system of chloroform and acetone in a volume ratio of 20:1, or dichloromethane and methanol in a volume ratio of 35:1, or petroleum ether and ethyl acetate in a volume ratio of 1:1; the liquid phase mobile phase selected by the reverse phase chromatographic column is acetonitrile and water in a volume ratio of 5:5, or methanol and water in a volume ratio of 6:4, or methanol and water in a volume ratio of 5:5, most preferably is acetonitrile:water=5:5; (2) dissolving a sample to be separated and purified with an eluent or a mobile phase, carrying out sample loading and elution, collecting the eluent, and spin-drying the sample to obtain the purified 4β-amino substituted podophyllotoxin derivatives products.

The in-vitro tests for inhibition of the cell activity of lung cancer HepG2, cervical cancer Hela, lung cancer A549 and breast cancer MCF7 show that the antitumor activity of the compound of formula (V) prepared by the invention is significantly improved compared with that of podophyllotoxin or 4'-demethylepipodophyllotoxin. The test result shows that the compound of formula (V) can be prepared into an antitumor drug and is clinically applied to antitumor treatment.

The antitumor pharmaceutical composition provided by the invention comprises an effective amount of a compound of formula (V) or a salt thereof and a pharmaceutically acceptable carrier, that is, the pharmaceutically acceptable amount of the compound of formula (V) or the salt thereof and the pharmaceutically acceptable carrier are formulated and prepared into any type of suitable pharmaceutical composition according to a conventional formulation method in the art. In general, the pharmaceutical compositions are suitable for oral and injectable administration, as well as other methods of administration, for example transdermal administration. The pharmaceutical compositions may be in the form of tablets, capsules, powders, granules, lozenges, suppositories, or liquid preparations such as oral liquids or sterile parenteral suspensions. The composition may be in the form of large or small volume injection, lyophilized powder injection, sterile powder subpackage and the like. In order to achieve consistency of administration, the pharmaceutical compositions of the present invention are preferably in a single dosage form. Single dose forms for oral administration may be tablets and capsules and may contain conventional excipients such as binding agents, for example syrup, acacia gum, gelatin, sorbitol, tragacanth or polyvinylpyrrolidone; fillers such as lactose, sugar, corn starch, calcium phosphate, sorbitol or glycine; tabletting lubricants such as magnesium stearate; disintegrants, such as starch, polyvinylpyrrolidone, sodium starch glycolate or microcrystalline cellulose, or pharmaceutically acceptable wetting agents, such as sodium lauryl sulfate.

BRIEF DESCRIPTION OF THE DRAWINGS

FIG. 1 is a structural formula of podophyllotoxin, 4'-demethylepipodophyllotoxin, I-podophyllotoxin and I-4'-demethylepipodophyllotoxin;

FIG. 2 is a structural formula of 1-aminoanthraquinone, 2-aminoanthraquinone, 1,2-diaminoanthraquinone, 1,5-diaminoanthraquinone, 2,6-diaminoanthraquinone, 2,4-quinazolinediamine, 6-aminoquinoline, 5-aminoquinoline, 5-aminoisoquinoline, 8-aminoquinoline, 8-aminoquinaldine, 5-indazolamine, 6-indazolamine, 7-indazolamine, 5-aminoindole, 6-aminoindole, 7-aminoindole, 2-(2-aminophenyl) benzimidazole and N-(5-amino-2-methylphenyl)-4-(3-pyridyl)-2-aminopyrimidine.

DETAILED DESCRIPTION OF THE INVENTION

Figure 3:
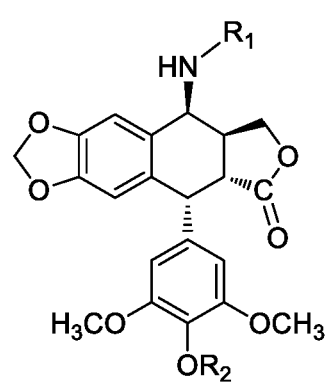
FIG. 3 is a compound of formula (V) of the present invention.

Hereinafter, the technical solution of the present invention will be further described below through specific examples.

The materials and equipment employed in the present invention, unless otherwise specified, are either commercially available or commonly used in the art, and the methods in the examples, unless otherwise specified, are conventional methods in the art.

Test Materials
1. Podophyllotoxin and 4'-demethylepipodophyllotoxin: both purchased from Xi'an Helin Bioengineering Co., Ltd.;
2. 1-aminoanthraquinone, 2-aminoanthraquinone, 1,2-diaminoanthraquinone, 1,5-diaminoanthraquinone, 2,6-diaminoanthraquinone, 2,4-quinazolinediamine, 6-aminoquinoline, 5-aminoquinoline, 5-aminoisoquinoline, 8-aminoquinoline, 8-aminoquinaldine, 5-indazolamine, 6-indazolamine, 7-indazolamine, 5-aminoindole, 6-aminoindole, 7-aminoindole, 2-(2-aminophenyl) benzimidazole and N-(5-amino-2-methylphenyl)-4-(3-pyridyl)-2-aminopyrimidine were purchased from Aladdin, J&K, and Bidepharm.

Example 1 Synthesis and Purification of 4β-NH-(1-Aminoanthraquinone) Podophyllotoxin Compound (1)

(1) Synthesis of 4β-NH-(1-aminoanthraquinone) podophyllotoxin: 414 mg (1 mmol) of podophyllotoxin and 149 mg (1 mmol) of NaI were dried for 1 h, then dissolved in 10 mL of acetonitrile, 0.45 mL (3.57 mmol) of boron trifluoride diethyl ether was dropwise added in a 0° C. ice bath, the mixture was stirred at 600 rpm for 1 h at room temperature, and then spun-dry to obtain I-podophyllotoxin; 524 mg (1 mmol) of I-podophyllotoxin and 223 mg (1 mmol) of 1-aminoanthraquinone were dissolved in 10 mL of tetrahydrofuran, 1 g (5.08 mmol) of $BaCO_3$ as a catalyst and 0.5 mL (3.61 mmol) of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst $BaCO_3$ was removed by filtration, and the filtrate was spun-dry to obtain crude 4β-NH-(1-aminoanthraquinone) podophyllotoxin.

(3) Separation and purification of 4β-NH-(1-aminoanthraquinone) podophyllotoxin:

Separation and purification were performed using silica gel column chromatography and preparative column chromatography, respectively:

(A) A separation was performed through a normal phase silica gel column (normal phase silica gel: China Qingdao Haiyang Chemical Co., Ltd., 0170021, 300-400 meshes); a chloroform:acetone=20:1 system was used as eluent, with the loading sample of 4 mL, and the constant flow rate of 2.0 ml/min; each 5 mL eluent was collected as a fraction. The fractions were examined by normal phase silica gel thin layer (German Merck high performance silica gel thin layer) or similar polar thin layer; a chloroform:acetone=20:1 system was used as a developing agent, and fractions corresponding to target spots were combined; and the combined samples were spun-dry to obtain 4β-NH-(1-aminoanthraquinone) podophyllotoxin, which was stored in a refrigerator of 4° C. in the dark condition.

(B) Preparation and separation were performed through a reverse chromatographic column (chromatographic column: YMC HPLC column, C-18, length 20 cm, inner diameter 15 mm); acetonitrile:water=5:5 system was used as a mobile phase, with a flow rate of 1.0 mL/min, and each loading sample of 0.2 mL, and the target product was collected according to the liquid chromatography peak at the retention time of 15 min. The collected mobile phase containing the target product was freeze-dried at low temperature to obtain a red powdery sample of 4β-NH-(1-aminoanthraquinone) podophyllotoxin, which was stored in a refrigerator of 4° C. in the dark condition.

Compound (1) 4β-NH-(1-aminoanthraquinone) podophyllotoxin, $C_{36}H_{29}NO_9$, red powder:

$^1$H NMR (300 MHz, $CDCl_3$): δ 10.04 (d, J=7.47 Hz, 1H), 8.24 (m, 2H), 7.75 (m, 3H), 7.65 (d, J=7.91 Hz, 1H), 7.08 (d, J=8.40 Hz, 1H), 6.79 (s, 1H), 6.59 (s, 1H), 6.37 (s, 2H), 5.98 (d, J=6.94 Hz, 2H), 5.06 (m, 1H), 4.72 (d, J=4.51 Hz, 1H), 4.41 (t, J=7.77 Hz, 1H), 3.90 (d, J=10.06 Hz, 2H), 3.83 (s, 3H), 3.78 (s, 6H), 3.26 (dd, J=14.11 Hz, 1H), 3.19-3.11 (m, 1H). $^{13}$C NMR (75 MHz, $CDCl_3$): δ 185.63, 183.23, 174.06, 152.56, 150.52, 148.47, 147.62, 137.19, 135.80, 134.98, 134.93, 134.45, 134.13, 133.40, 132.73, 131.75, 129.19, 126.78, 126.69, 116.70, 116.44, 113.46, 109.96, 109.17, 108.23, 101.53, 68.20, 60.69, 56.20, 51.18, 43.57, 41.87, 38.28. ESI-MS m/z: 620.61[M+H]$^+$

Example 2 Synthesis and Purification of 4β-NH-(2-Aminoanthraquinone) Podophyllotoxin Compound (2)

(1) Synthesis of 4β-NH-(2-aminoanthraquinone) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 223 mg of 2-aminoanthraquinone were dissolved in 10 mL of tetrahydrofuran, 1 g of $BaCO_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO$_3$ was removed by filtration, and the filtrate was spun-dry to obtain crude 4β-NH-(2-aminoanthraquinone) podophyllotoxin.

(3) Separation and purification of 4β-NH-(2-aminoanthraquinone) podophyllotoxin:

Separation and purification were performed using silica gel column chromatography and preparative column chromatography, respectively, in the same manner as in Example 1.

Compound (2) 4β-NH-(2-aminoanthraquinone) podophyllotoxin, C$_{36}$H$_{29}$NO$_9$, red powder:

$^1$H NMR (300 MHz, CDCl$_3$): δ 8.35-8.20 (m, 2H), 8.18 (d, J=8.56 Hz, 1H), 7.78-7.70 (m, 3H), 7.35 (d, J=2.52 Hz, 1H), 6.89 (dd, J=8.60 Hz, 1H), 6.76 (s, 1H), 6.55 (s, 1H), 6.31 (s, 2H), 5.98 (d, J=6.60 Hz, 2H), 5.48 (s, 1H), 4.98 (dd, J=6.31 Hz, 1H), 4.64 (d, J=4.38 Hz, 1H), 4.47 (dd, J=10.49 Hz, 1H), 3.93-3.89 (m, 1H), 3.82 (s, 3H), 3.77 (s, 6H), 3.13-3.11 (m, 2H). $^{13}$C NMR (75 MHz, CDCl$_3$): δ 178.92, 176.73, 169.32, 147.95, 146.83, 143.93, 143.09, 132.62, 130.93, 129.84, 129.51, 129.17, 128.67, 125.38, 124.96, 124.20, 122.34, 122.27, 119.96, 105.37, 104.32, 103.44, 96.97, 63.62, 56.02, 51.53, 47.38, 38.84, 37.09, 33.65. ESI-MS m/z: 620.18 [M+H]$^+$

Example 3 Synthesis and Purification of 4β-NH-(1,2-Diaminoanthraquinone) Podophyllotoxin Compound (3)

(1) Synthesis of 4β-NH-(1,2-diaminoanthraquinone) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 238 mg of 1,2-diaminoanthraquinone were dissolved in 10 mL of tetrahydrofuran, 1 g of BaCO3 as a catalyst and 0.5 mL of triethylamine as an acid binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(1,2-diaminoanthraquinone) podophyllotoxin.

(3) Separation and purification of 4β-NH-(1,2-diaminoanthraquinone) podophyllotoxin:

Separation and purification were performed using silica gel column chromatography and preparative column chromatography, respectively, in the same manner as in Example 1.

Compound (3) 4β-NH-(1,2-diaminoanthraquinone) podophyllotoxin, C$_{36}$H$_{30}$N$_2$O$_9$, amaranth powder:

$^1$H NMR (400 MHz, CDCl$_3$): δ 8.22 (d, J=6.82 Hz, 1H), 8.00 (d, J=8.29 Hz, 1H), 7.90-7.64 (m, 5H), 7.09 (d, J=8.24 Hz, 1H), 6.50 (s, 1H), 6.29 (s, 2H), 5.82 (s, 1H), 5.69 (s, 1H), 5.22 (s, 1H), 4.73-4.72 (m, 1H), 4.35 (s, 2H), 3.80 (s, 3H), 3.73 (s, 6H), 3.49 (dd, J=12.71 Hz, 1H), 3.20~3.08 (m, 1H). $^{13}$C NMR (100 MHz, CDCl$_3$): δ 187.05, 182.19, 174.75, 152.75, 148.15, 146.47, 141.16, 140.23, 134.20, 133.50, 133.66, 133.32, 133.10, 132.10, 130.62, 128.91, 126.79, 125.05, 121.00, 113.54, 119.71, 108.69, 108.47, 111.16, 101.27, 67.97, 61.00, 56.45, 52.75, 41.50, 37.64, 29.94. ESI-MS m/z: 635.18[M+H]$^+$

Example 4 Synthesis and Purification of 4β-NH-(1,5-Diaminoanthraquinone) Podophyllotoxin Compound (4)

(1) Synthesis of 4β-NH-(1,5-diaminoanthraquinone) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 238 mg of 1,5-diaminoanthraquinone were dissolved in 10 mL of acetone, 1 g of BaCO$_3$ as a catalyst and 0.5 mL of pyridine as an acid binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(1,5-diaminoanthraquinone) podophyllotoxin.

(3) Separation and purification of 4β-NH-(1,5-diaminoanthraquinone) podophyllotoxin:

Separation and purification were performed using silica gel column chromatography and preparative column chromatography, respectively, in the same manner as in Example 1.

Compound (4) 4β-NH-(1,5-diaminoanthraquinone) podophyllotoxin, C$_{36}$H$_{30}$N$_2$O$_9$, red powder:

$^1$H NMR (400 MHz, CDCl$_3$): δ 10.01 (d, J=10.01 Hz, 1H), 7.68 (d, J=7.70 Hz, 1H), 7.62 (t, J=7.97 Hz, 1H), 7.53 (d, J=7.39 Hz, 1H), 7.44 (d, J=7.88 Hz, 1H), 6.97 (m, 2H), 6.79 (s, 1H), 6.57 (s, 1H), 6.36 (s, 2H), 5.98 (d, J=8.26 Hz, 2H), 5.02 (s, 1H), 4.70 (s, 1H), 4.40 (t, J=7.90 Hz, 1H), 3.87 (d, J=9.82 Hz, 2H), 3.80 (s, 3H), 3.80 (m, 6H), 3.25 (d, J=14.46 Hz, 1H), 3.16-3.06 (m, 1H). $^{13}$C NMR (100 MHz, CDCl$_3$): δ 186.00, 185.04, 174.28, 150.79, 150.38, 148.47, 147.62, 146.45, 136.50, 135.71, 135.49, 134.81, 134.11, 131.95, 130.53, 129.39, 122.22, 116.68, 116.10, 115.27, 113.67, 113.34, 110.01, 109.26, 108.00, 101.54, 68.33, 56.50, 56.50, 51.23, 43.48, 42.06, 38.34. ESI-MS m/z: 635.19[M+H]$^+$

Example 5 Synthesis and Purification of 4β-NH-(2,6-Diaminoanthraquinone) Podophyllotoxin Compound (5)

(1) Synthesis of 4β-NH-(2,6-diaminoanthraquinone) podophyllotoxin: 414 mg (1 mmol) of podophyllotoxin and 166 mg (1 mmol) of KI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 238 mg of 2,6-diaminoanthraquinone were dissolved in 10 mL of chloroform, 1 g of BaCO$_3$ as a catalyst and 0.5 mL of triethylamine as an acid binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(2,6-diaminoanthraquinone) podophyllotoxin.

(3) Separation and purification of 4β-NH-(2,6-diaminoanthraquinone) podophyllotoxin:

Separation and purification were performed using silica gel column chromatography and preparative column chromatography, respectively, in the same manner as in Example 1.

Compound (5) 4β-NH-(2,6-diaminoanthraquinone) podophyllotoxin, $C_{36}H_{30}N_2O_9$, yellow powder:

$^1$H NMR (400 MHz, CDCl$_3$): δ 8.13 (d, J=8.52 Hz, 1H), 8.09 (d, J=8.42 Hz, 1H), 7.43 (d, J=2.47 Hz, 1H), 7.36 (d, J=2.47 Hz, 1H), 6.90 (dd, J=8.41 Hz, 1H), 6.83 (dd, J=8.56 Hz, 1H), 6.76 (s, 1H), 6.54 (s, 1H), 6.32 (s, 2H), 5.97 (dd, J=9.34 Hz, 2H), 4.98 (dd, J=7.29 Hz, 1H), 4.62 (dd, J=10.07 Hz, 2H), 4.47 (dd, J=10.33 Hz, 1H), 4.30 (t, J=6.73 Hz, 1H), 3.91 (dd, J=15.72 Hz, 2H), 3.82 (s, 3H), 3.77 (s, 6H), 3.12 (m, 2H). $^{13}$C NMR (100 MHz, CDCl$_3$): δ 177.25, 177.22, 169.40, 147.94, 147.27, 146.85, 143.87, 143.05, 132.58, 131.60, 131.28, 129.89, 127.53, 127.34, 126.14, 125.17, 125.14, 124.34, 124.06, 120.02, 119.68, 113.48, 106.49, 105.32, 103.42, 96.94, 63.70, 56.02, 51.51, 47.32, 38.85, 37.09, 33.66. ESI-MS m/z: 657.19[M+Na]$^+$

Example 6 Synthesis and Purification of 4β-NH-(2,4-Quinazolinediamine) Podophyllotoxin Compound (6)

(1) Synthesis of 4β-NH-(2,4-quinazolinediamine) podophyllotoxin: 414 mg (1 mmol) of podophyllotoxin and 166 mg (1 mmol) of KI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 160 mg of 2,4-quinazolinediamine were dissolved in 10 mL of ethanol, 1 g of BaCO$_3$ as a catalyst and 0.5 mL of pyridine as an acid-binding agent were added, the mixture was stirred at 600 rpm for 2 h in a 0° C. ice bath, then stirred at 600 rpm for 14 h at 27° C. room temperature, a chloroform:acetone=20:1 system was used as a developing solvent to monitor the end of the reaction.

(2) The catalyst BaCO$_3$ was removed by filtration, and the filtrate was spun-dry to obtain crude 4β-NH-(2,4-quinazolinediamine) podophyllotoxin.

(3) Separation and purification of 4β-NH-(2,4-quinazolinediamine) podophyllotoxin:

Separation and purification were performed using silica gel column chromatography and preparative column chromatography, respectively, in the same manner as in Example 1.

Compound (6) 4β-NH-(2,4-quinazolinediamine) podophyllotoxin, $C_{30}H_{28}N_4O_7$, white powder:

$^1$H NMR (400 MHz, CDCl$_3$): δ 7.59 (m, 2H), 7.46 (d, J=6.31 Hz, 1H), 7.18 (d, J=6.951H), 6.84 (s, 1H), 6.44 (s, 1H), 6.32 (s, 2H), 5.88 (d, J=18.42 Hz, 2H), 5.47 (d, J=23.47 Hz, 3H), 5.47 (s, 3H), 4.58 (d, J=3.70 Hz, 1H), 4.47 (m, 1H), 3.95 (t, J=9.37 Hz, 1H), 3.81 (s, 3H), 3.75 (s, 6H), 3.10 (m, 2H). $^{13}$C NMR (100 MHz, CDCl$_3$): δ 174.94, 161.94, 158.29, 152.46, 1487.96, 147.21, 146.41, 133.89, 133.59, 132.21, 130.75, 130.09, 122.03, 121.94, 109.73, 109.32, 107.89, 101.34, 69.78, 60.65, 56.15, 49.78, 43.74, 41.86, 38.14. ESI-MS m/z: 555.56[M+H]$^-$

Example 7 Synthesis and Purification of 4β-NH-(6-Aminoquinoline) Podophyllotoxin Compound (7)

(1) Synthesis of 4β-NH-(6-aminoquinoline) podophyllotoxin: 414 mg (1 mmol) of podophyllotoxin and 166 mg (1 mmol) of KI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 144 mg of 6-aminoquinoline were dissolved in 10 mL of acetonitrile, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(6-aminoquinoline) podophyllotoxin.

(3) Separation and purification of 4β-NH-(6-aminoquinoline) podophyllotoxin:

Separation and purification were performed using silica gel column chromatography and preparative column chromatography, respectively, in the same manner as in Example 1.

Compound (7) 4β-NH-(6-aminoquinoline) podophyllotoxin, $C_{31}H_{28}N_2O_7$, light yellow powder:

$^1$H NMR (400 MHz, CDCl$_3$): δ 8.64 (d, J=3.26 Hz, 1H), 7.91 (t, J=8.44 Hz, 2H), 7.30 (dd, J=8.28 Hz, 1H), 7.06 (dd, J=9.02 Hz, 1H), 6.79 (s, 1H), 6.65 (d, J=2.43 Hz, 1H), 6.54 (s, 1H), 6.33 (s, 2H), 5.96 (d, J=6.47 Hz, 2H), 4.83 (m, 1H), 4.62 (d, J=4.74 Hz, 1H), 4.44 (m, 1H), 4.28 (d, J=5.96 Hz, 1H), 3.99 (m, 1H), 3.81 (s, 3H), 3.74 (s, 6H), 3.18 (dd, J=14.04 Hz, 1H), 3.13-3.04 (m, 1H). $^{13}$C NMR (100 MHz, CDCl$_3$): δ 174.56, 152.63, 148.40, 147.71, 146.79, 145.34, 143.38, 137.31, 134.99, 133.88, 131.88, 130.85, 130.03, 121.79, 120.86, 117.92, 109.96, 109.16, 108.31, 102.56, 101.60, 68.82, 60.75, 56.29, 52.62, 43.57, 42.01, 38.62. ESI-MS m/z: 541.18[M+H]$^+$

Example 8 Synthesis and Purification of 4β-NH-(5-Aminoquinoline) Podophyllotoxin Compound (8)

(1) Synthesis of 4β-NH-(5-aminoquinoline) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 144 mg of 5-aminoquinoline were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(5-aminoquinoline) podophyllotoxin.

(3) Separation and purification of 4β-NH-(5-aminoquinoline) podophyllotoxin:

Separation and purification were performed using silica gel column chromatography and preparative column chromatography, respectively, in the same manner as in Example 1.

Compound (8) 4β-NH-(5-aminoquinoline) podophyllotoxin, $C_{31}H_{28}N_2O_7$, light yellow powder:

$^1$H NMR (400 MHz, CDCl$_3$): δ 8.84 (d, J=3.63 Hz, 1H), 8.16 (d, J=8.45 Hz, 1H), 7.58-7.52 (m, 2H), 7.29 (dd, J=8.53

Hz, 1H), 6.75 (s, 1H), 6.56 (d, J=6.87 Hz, 1H), 6.53 (s, 1H), 6.32 (s, 2H), 5.94 (d, J=4.58 Hz, 2H), 4.91 (t, J=4.43 Hz, 1H), 4.69 (d, J=5.04 Hz, 1H), 4.61 (d, J=4.89 Hz, 1H), 4.41 (t, J=7.98 Hz, 1H), 3.90 (dd, J=10.34 Hz, 1H), 3.79 (s, 3H), 3.74 (s, 6H), 3.24 (dd, J=14.03 Hz, 1H), 3.13-3.04 (m, 1H). $^{13}$C NMR (100 MHz, CDCl$_3$): δ 174.50, 152.60, 150.30, 149.14, 148.42, 147.76, 142.86, 137.20, 135.02, 132.12, 130.10, 130.04, 128.68, 119.73, 119.59, 117.92, 109.98, 109.17, 108.22, 103.95, 101.61, 68.92, 60.75, 56.25, 52.62, 43.59, 42.09, 38.56. ESI-MS m/z: 541.56[M+H]$^+$

Example 9 Synthesis and Purification of 4β-NH-(5-Aminoisoquinoline) Podophyllotoxin Compound (9)

(1) Synthesis of 4β-NH-(5-aminoisoquinoline) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 144 mg of 5-aminoisoquinoline were dissolved in 10 mL of tetrahydrofuran, 1 g of BaCO$_3$ as a catalyst and 0.5 mL of triethylamine as an acid binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(5-aminoisoquinoline) podophyllotoxin.

(3) Separation and purification of 4β-NH-(5-aminoisoquinoline) podophyllotoxin:

Separation and purification were performed using silica gel column chromatography and preparative column chromatography, respectively, in the same manner as in Example 1.

Compound (9) 4β-NH-(5-aminoisoquinoline) podophyllotoxin, C$_{31}$H$_{28}$N$_2$O$_7$, light yellow powder:

$^1$H NMR (400 MHz, CDCl$_3$): δ 9.16 (s, 1H), 8.44 (d, J=8.0 Hz, 1H), 7.53-7.46 (m, 2H), 7.40 (d, J=8 Hz, 1H), 6.74 (s, 1H), 6.70 (d, J=4.1 Hz, 1H), 6.56 (s, 1H), 6.50 (s, 1H), 6.34 (s, 2H), 5.95 (t, 2H), 4.90 (t, 1H), 4.64 (t, 2H), 4.43 (t, 1H), 3.94-3.87 (m, 1H), 3.80 (s, 3H), 3.76 (m, 6H), 3.27 (dd, J=12.0 Hz, 1H), 3.16-3.09 (m, 1H). $^{13}$C NMR (100 MHz, CDCl$_3$): δ 174.50, 152.94, 152.63, 148.52, 147.83, 142.39, 141.75, 137.26, 134.97, 135.15, 129.97, 127.79, 125.49, 117.49, 113.17, 110.06, 109.10, 108.26, 106.89, 101.65, 68.81, 60.76, 56.28, 52.56, 43.59, 42.09, 38.60. ESI-MS m/z: 563.56[M+Na]$^+$

Example 10 Synthesis and Purification of 4β-NH-(8-Aminoquinoline) Podophyllotoxin Compound (10)

(1) Synthesis of 4β-NH-(8-aminoquinoline) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 144 mg of 8-aminoquinoline were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(8-aminoquinoline) podophyllotoxin.

(3) Separation and purification of 4β-NH-(8-aminoquinoline) podophyllotoxin:

Separation and purification were performed using silica gel column chromatography and preparative column chromatography, respectively, in the same manner as in Example 1.

Compound (10) 4β-NH-(8-aminoquinoline) podophyllotoxin, C$_{31}$H$_{28}$N$_2$O$_7$, light yellow powder:

$^1$H NMR (400 MHz, CDCl$_3$): δ 8.67 (dd, J=4.0 Hz, 1H), 8.08 (dd, J=4.0 Hz, 1H), 7.40-7.36 (m, 2H), 7.14 (d, J=8 Hz, 1H), 6.78 (s, 1H), 6.59 (d, J=7.52 Hz, 1H), 6.56 (s, 1H), 6.55 (s, 1H), 6.45 (d, J=6.77 Hz, 1H), 6.38 (s, 2H), 5.92 (dt, J=4.71 Hz, 2H), 4.87 (dd, J=6.39 Hz, 1H), 4.66 (d, J=4.98 Hz, 1H), 4.43 (t, J=7.99 Hz, 1H), 3.97 (dd, J=10.74 Hz, 1H), 3.81 (s, 3H), 3.77 (s, 6H), 3.27 (dd, J=14.08 Hz, 1H), 3.16-3.07 (m, 1H). $^{13}$C NMR (100 MHz, CDCl$_3$): δ 174.50, 152.59, 148.24, 147.58, 147.29, 144.05, 137.67, 137.22, 136.14, 135.32, 131.83, 130.48, 128.74, 127.42, 121.83, 115.34, 109.81, 109.51, 108.37, 104.10, 101.46, 68.95, 60.76, 56.28, 52.23, 43.68, 42.08, 39.00. ESI-MS m/z: 541.56[M+H]$^+$

Example 11 Synthesis and Purification of 4β-NH-(8-Aminoquinaldine) Podophyllotoxin Compound (11)

(1) Synthesis of 4β-NH-(8-aminoquinaldine) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 158 mg of 8-aminoquinaldine were dissolved in 10 mL of tetrahydrofuran, 1 g of BaCO$_3$ as a catalyst and 0.5 mL of triethylamine as an acid binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(8-aminoquinaldine) podophyllotoxin.

(3) Separation and purification of 4β-NH-(8-aminoquinaldine) podophyllotoxin:

Separation and purification were performed using silica gel column chromatography and preparative column chromatography, respectively, in the same manner as in Example 1.

Compound (11) 4β-NH-(8-aminoquinaldine) podophyllotoxin, C$_{32}$H$_{30}$N$_2$O$_7$, white powder:

$^1$H NMR (400 MHz, CDCl$_3$): δ 7.96 (d, J=8.38 Hz, 1H), 7.32 (t, J=7.88 Hz, 1H), 7.27 (d, J=8.40 Hz, 1H), 7.10 (d, J=7.77 Hz, 1H), 6.56 (m, 2H), 6.48 (d, J=5.95 Hz, 1H), 6.38 (s, 2H), 5.96 (s, 2H), 4.87 (dd, J=6.42 Hz, 1H), 4.68 (d, J=4.96 Hz, 1H), 4.42 (t, J=8.02 Hz, 1H), 3.96 (m, 1H), 3.84 (s, 1H), 3.82 (s, 3H), 3.78 (s, 6H), 3.33 (dd, J=14.08 Hz, 1H), 3.16-3.07 (m, 1H), 2.64 (s, 3H). $^{13}$C NMR (100 MHz, CDCl$_3$): δ 174.82, 156.31, 152.59, 148.17, 147.54, 143.57, 137.22, 136.98, 136.17, 135.34, 131.87, 130.68, 126.71, 126.28, 122.64, 115.19, 109.83, 109.64, 108.37, 104.12, 101.46, 69.02, 60.76, 56.29, 52.16, 43.73, 42.16, 39.02, 25.17. ESI-MS m/z: 555.20[M+H]$^+$

Example 12 Synthesis and Purification of 4β-NH-(5-Indazolamine) Podophyllotoxin Compound (12)

(1) Synthesis of 4β-NH-(5-indazolamine) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 133 mg of 5-indazolamine were dissolved in 10 mL of tetrahydrofuran, 1 g of BaCO$_3$ as a catalyst and 0.5 mL of triethylamine w as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing solvent to monitor the reaction endpoint.

(2) The catalyst BaCO$_3$ was removed by filtration, and the filtrate was spun-dry to obtain crude 4β-NH-(5-indazolamine) podophyllotoxin.

(3) Separation and purification of 4β-NH-(5-indazolamine) podophyllotoxin:

Separation and purification were performed using silica gel column chromatography and preparative column chromatography, respectively, in the same manner as in Example 1.

Compound (12) 4β-NH-(5-indazolamine) podophyllotoxin, C$_{29}$H$_{27}$N$_3$O$_7$, white powder:

$^1$H NMR (400 MHz, CDCl$_3$): δ 7.89 (s, 1H), 7.32 (d, J=8.0 Hz, 1H), 7.39 (s, 1H), 6.76 (s, 1H), 6.75-6.73 (m, 2H), 6.69 (d, J=4 Hz, 1H), 6.50 (s, 1H), 6.33 (s, 2H), 5.93 (dd, J=6.0 Hz, 2H), 4.68 (s, 1H), 4.58 (d, J=4.0 Hz, 1H), 4.42 (t, 1H), 3.94-3.90 (m, 1H), 3.80 (s, 3H), 3.74 (m, 6H), 3.20 (dd, J=14.0 Hz, 1H), 3.08-2.99 (m, 1H). $^{13}$C NMR (100 MHz, CDCl$_3$): δ 175.05, 152.57, 148.16, 147.57, 142.36, 137.17, 135.40, 135.26, 133.25, 131.66, 130.83, 129.90, 118.12, 111.33, 109.87, 109.13, 108.29, 101.51, 98.04, 69.12, 60.75, 56.25, 53.36, 43.58, 41.97, 38.77. ESI-MS m/z: 530.54[M+H]$^+$

Example 13 Synthesis and Purification of 4β-NH-(6-Indazolamine) Podophyllotoxin Compound (13)

(1) Synthesis of 4β-NH-(6-indazolamine) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 133 mg of 6-indazolamine were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing solvent to monitor the reaction endpoint.

(2) The catalyst BaCO$_3$ was removed by filtration, and the filtrate was spun-dry to obtain crude 4β-NH-(6-indazolamine) podophyllotoxin.

(3) Separation and purification of 4β-NH-(6-indazolamine) podophyllotoxin:

Separation and purification were performed using silica gel column chromatography and preparative column chromatography, respectively, in the same manner as in Example 1.

Compound (13) 4β-NH-(6-indazolamine) podophyllotoxin, C$_{29}$H$_{27}$N$_3$O$_7$, white powder:

$^1$H NMR (400 MHz, CDCl$_3$): δ 8.01 (s, 1H), 7.30 (d, J=8.0 Hz, 1H), 7.35 (s, 1H), 6.71 (s, 1H), 6.73 (m, 2H), 6.64 (d, J=4 Hz, 1H), 6.47 (s, 1H), 6.30 (s, 2H), 5.91 (dd, J=4.90 Hz, 2H), 4.64 (s, 1H), 4.52 (d, J=4.0 Hz, 1H), 4.37 (t, 1H), 3.91 (m, 1H), 3.80 (s, 3H), 3.78 (m, 6H), 3.24 (dd, J=14.0 Hz, 1H), 3.04 (m, 1H). $^{13}$C NMR (100 MHz, CDCl$_3$): δ 175.15, 152.50, 148.56, 147.77, 142.46, 137.24, 135.30, 135.21, 133.29, 131.62, 130.82, 129.94, 118.02, 111.13, 109.85, 109.12, 108.25, 101.50, 98.01, 69.10, 60.74, 56.25, 53.34, 43.51, 42.04, 38.79. ESI-MS m/z: 530.52, [M+H]$^+$

Example 14 Synthesis and Purification of 4β-NH-(7-Indazolamine) Podophyllotoxin Compound (14)

(1) Synthesis of 4β-NH-(7-indazolamine) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 133 mg of 7-indazolamine were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing solvent to monitor the end of the reaction.

(2) The catalyst BaCO$_3$ was removed by filtration, and the filtrate was spun-dry to obtain crude 4β-NH-(7-indazolamine) podophyllotoxin.

(3) Separation and purification of 4β-NH-(7-indazolamine) podophyllotoxin:

Separation and purification were performed using silica gel column chromatography and preparative column chromatography, respectively, in the same manner as in Example 1.

Compound (14) 4β-NH-(7-indazolamine) podophyllotoxin, C$_{29}$H$_{27}$N$_3$O$_7$, white powder:

$^1$H NMR (400 MHz, CDCl$_3$): δ 7.80 (s, 1H), 7.39 (s, 1H), 7.30 (d, J=4.0 Hz, 1H), 6.71 (s, 1H), 6.73 (m, 2H), 6.62 (d, J=4.01 Hz, 1H), 6.43 (s, 1H), 6.30 (s, 2H), 5.85 (dd, J=6.0 Hz, 2H), 4.65 (s, 1H), 4.51 (d, J=4.10 Hz, 1H), 4.40 (t, 1H), 3.92 (m, 1H), 3.72 (s, 3H), 3.79 (m, 6H), 3.22 (dd, J=14.0 Hz, 1H), 3.05-2.99 (m, 1H). $^{13}$C NMR (100 MHz, CDCl$_3$): δ 174.95, 152.27, 148.36, 147.47, 142.32, 137.12, 135.41, 135.20, 133.21, 131.59, 130.80, 129.82, 118.10, 111.28, 109.84, 109.10, 108.22, 101.50, 98.08, 69.10, 60.79, 56.28, 53.39, 43.58, 42.05, 38.79. ESI-MS m/z: 530.53, [M+H]$^+$

Example 15 Synthesis and Purification of 4β-NH-(5-Aminoindole) Podophyllotoxin Compound (15)

(1) Synthesis of 4β-NH-(5-aminoindole) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 132 mg of 5-aminoindole were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(5-aminoindole) podophyllotoxin.

(3) Separation and purification of 4β-NH-(5-aminoindole) podophyllotoxin:

Separation and purification were performed using silica gel column chromatography and preparative column chromatography, respectively, in the same manner as in Example 1.

Compound (15) 4β-NH-(5-aminoindole) podophyllotoxin, $C_{30}H_{28}N_2O_7$, black powder:

$^1$H NMR (400 MHz, CDCl$_3$): δ 8.33 (s, 1H), 7.40 (d, J=8.05 Hz, 1H), 7.06 (m, 1H), 6.71 (s, 1H), 6.52 (d, J=12.11 Hz, 2H), 6.44 (s, 1H), 6.37 (s, 1H), 6.35 (s, 2H), 5.96 (dd, J=5.20 Hz, 2H), 4.82 (dd, 8.1, 16.2 Hz, 1H), 4.70 (d, J=0.35 Hz, 1H), 4.35 (t, 1H), 4.06-3.94 (m, 1H), 3.77 (s, 3H), 3.75 (s, 6H), 3.16 (dd, J=12.0 Hz, 1H), 3.04-2.93 (m, 1H). $^{13}$C NMR (100 MHz, CDCl$_3$): δ 174.25, 148.04, 147.38, 146.64, 139.74, 137.22, 134.01, 131.62, 131.41, 130.58, 122.79, 121.82, 120.95, 109.85, 109.17, 108.05, 102.45, 101.47, 92.76, 69.27, 56.52, 53.47, 43.45, 42.11, 38.80. ESI-MS m/z: 529.55, [M+H]$^+$.

Example 16 Synthesis and Purification of 4β-NH-(6-Aminoindole) Podophyllotoxin Compound (16)

(1) Synthesis of 4β-NH-(6-aminoindole) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 132 mg of 6-aminoindole were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction end point.

(2) The catalyst BaCO$_3$ was removed by filtration, and the filtrate was spun-dry to obtain crude 4β-NH-(6-aminoindole) podophyllotoxin.

(3) Separation and purification of 4β-NH-(6-aminoindole) podophyllotoxin:

Separation and purification were performed using silica gel column chromatography and preparative column chromatography, respectively, in the same manner as in Example 1.

Compound (16) 4β-NH-(6-aminoindole) podophyllotoxin, $C_{30}H_{28}N_2O_7$, black powder:

$^1$H NMR (400 MHz, CDCl$_3$): δ 8.13 (s, 1H), 7.43 (d, J=8.45 Hz, 1H), 7.03 (m, 1H), 6.77 (s, 1H), 6.5 (d, J=36.31 Hz, 2H), 6.45 (s, 2H), 6.36 (s, 1H), 6.33 (s, 2H), 5.93 (dd, J=5.70 Hz, 2H), 4.81 (dd, 10.08, 20.04 Hz, 1H), 4.68 (d, J=0.35 Hz, 1H), 4.34 (t, 1H), 4.06-3.95 (m, 1H), 3.79 (s, 3H), 3.77 (s, 6H), 3.18 (dd, J=14.0 Hz, 1H), 3.03-2.94 (m, 1H). $^{13}$C NMR (100 MHz, CDCl$_3$): δ 175.25, 148.08, 147.48, 146.44, 149.94, 137.12, 134.06, 131.69, 131.11, 130.88, 122.29, 121.62, 120.89, 109.80, 109.17, 108.07, 102.41, 101.45, 92.75, 69.26, 56.50, 53.32, 43.42, 42.01, 38.82. ESI-MS m/z: 529.52[M+H]$^+$

Example 17 Synthesis and Purification of 4β-NH-(7-Aminoindole) Podophyllotoxin Compound (17)

(1) Synthesis of 4β-NH-(7-aminoindole) podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 132 mg of 7-aminoindole were dissolved in 10 mL of tetrahydrofuran, 1 g of BaCO$_3$ d as a catalyst and 0.5 mL of triethylamine as an acid binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO$_3$ was removed by filtration, and the filtrate was spun-dry to obtain crude 4β-NH-(7-aminoindole) podophyllotoxin.

(3) Separation and purification of 4β-NH-(7-aminoindole) podophyllotoxin:

Separation and purification were performed using silica gel column chromatography and preparative column chromatography, respectively, in the same manner as in Example 1.

Compound (17) 4β-NH-(7-aminoindole) podophyllotoxin, $C_{30}H_{28}N_2O_7$, black powder:

$^1$H NMR (400 MHz, CDCl$_3$): δ 8.10 (s, 1H), 7.42 (d, J=8.25 Hz, 1H), 7.00 (m, 1H), 6.74 (s, 1H), 6.48 (d, J=16.30 Hz, 2H), 6.40 (s, 1H), 6.34 (s, 1H), 6.30 (s, 2H), 5.91 (dd, J=4.70 Hz, 2H), 4.81 (d, 12.04 Hz, 1H), 4.65 (d, J=0.35 Hz, 1H), 4.32 (t, 1H), 4.09-3.97 (m, 1H), 3.80 (s, 3H), 3.78 (s, 6H), 3.15 (dd, J=14.0 Hz, 1H), 3.05-2.96 (m, 1H). $^{13}$C NMR (100 MHz, CDCl$_3$): δ 175.05, 148.02, 147.44, 146.43, 139.84, 137.42, 134.16, 131.62, 131.10, 130.85, 122.27, 121.60, 120.86, 109.81, 109.13, 108.00, 102.40, 101.44, 92.72, 69.23, 56.47, 53.3, 43.46, 42.00, 38.76. ESI-MS m/z: 529.54, [M+H]$^+$.

Example 18 Synthesis and Purification of 4β-NH-(2-(2-aminophenyl) benzimidazole)-podophyllotoxin Compound (18)

(1) Synthesis of 4β-NH-(2-(2-aminophenyl) benzimidazole)-podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 209 mg of 2-(2-aminophenyl) benzimidazole were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing solvent to monitor the end of the reaction.

(2) The catalyst BaCO₃ was removed by filtration, and the filtrate was spun-dry to obtain crude 4β-NH-(2-(2-aminophenyl) benzimidazole)-podophyllotoxin.

(3) Separation and purification of 4β-NH-(2-(2-aminophenyl) benzimidazole)-podophyllotoxin:

Separation and purification were performed using silica gel column chromatography and preparative column chromatography, respectively, in the same manner as in Example 1.

Compound (18) 4β-NH-(2-(2-aminophenyl) benzimidazole)-podophyllotoxin, $C_{35}H_{31}N_3O_7$, white powder:

$^1$H NMR (400 MHz, CDCl₃): δ 10.34 (d, J=4 Hz, 1H), 9.42 (d, J=4 Hz, 1H), 7.66 (d, J=4 Hz, 1H), 7.53 (d, J=8 Hz, 1H), 7.31 (dd, J=12.0 Hz, 2H), 7.16 (m, 2H), 6.77 (d, J=12.0 Hz, 2H), 6.75-6.73 (m, 1H), 6.51 (s, 1H), 6.38 (s, 2H), 5.89 (s, 1H), 5.83 (s, 1H), 4.95 (dd, J=8 Hz, 1H), 4.67 (d, J=4.0 Hz, 1H), 4.35 (t, 1H), 3.97-3.92 (m, 1H), 3.84 (s, 3H), 3.75 (s, 6H), 3.36 (dd, J=14.0 Hz, 1H), 3.12~3.03 (m, 1H). $^{13}$C NMR (100 MHz, CDCl₃): δ 175.17, 152.57, 151.76, 148.16, 147.38, 147.23, 142.89, 137.00, 135.70, 132.89, 131.34, 131.26, 130.55, 127.52123.20, 122.07, 119.01, 116.23, 111.35, 110.68, 110.47, 109.61, 109.56, 108.37, 101.36, 69.00, 60.81, 56.25, 51.48, 43.72, 42.21, 38.98. ESI-MS m/z: 606.20[M+H]⁺

Example 19 Synthesis and Purification of 4β-NH-(2-(5-amino-2-methylphenyl)-4-(3-pyridyl) pyrimidine)-podophyllotoxin Compound (19)

(1) Synthesis of 4β-NH-(2-(5-amino-2-methylphenyl)-4-(3-pyridyl) pyrimidine)-podophyllotoxin: 414 mg (1 mmol) of podophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-podophyllotoxin; 524 mg of I-podophyllotoxin and 277 mg of 2-(5-amino-2-methylphenyl)-4-(3-pyridyl) pyrimidine were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(2-(5-amino-2-methylphenyl)-4-(3-pyridine) pyrimidine)-podophyllotoxin.

Separation and purification of 4β-NH-(2-(5-amino-2-methylphenyl)-4-(3-pyridyl) pyrimidine)-podophyllotoxin:

Separation and purification were performed using silica gel column chromatography and preparative column chromatography, respectively, in the same manner as in Example 1.

Compound (19) 4β-NH-(2-(5-amino-2-methylphenyl)-4-(3-pyridyl) pyrimidine)-podophyllotoxin, $C_{38}H_{35}N_5O_7$, white powder:

$^1$H NMR (400 MHz, CDCl₃): δ 9.22 (s, 1H), 8.62 (d, J=4.70 Hz, 1H), 8.42 (d, J=5.12 Hz, 1H), 8.27 (dd, J=8.01 Hz, 1H), 7.69 (d, J=2.21 Hz, 1H), 7.34 (dd, J=7.94 Hz, 1H), 7.09 (d, J=4.29 Hz, 2H), 7.03 (d, J=8.15 Hz, 1H), 6.78 (s, 1H), 6.47 (s, 1H), 6.31 (s, 2H), 6.24 (dd, J=8.13 Hz, 1H), 5.87 (d, J=16.22 Hz, 2H), 4.68 (t, J=4.42 Hz, 1H), 4.52 (d, J=4.89 Hz, 1H), 4.32 (t, J=7.93 Hz, 1H), 4.07 (d, J=4.62 Hz, 1H), 4.01 (m, 1H), 3.79 (s, 1H), 3.74 (s, 6H), 3.07 (dd, J=14.01 Hz, 1H), 2.99-2.90 (m, 1H), 2.28 (s, 3H). $^{13}$C NMR (400 MHz, CDCl₃): δ 174.99, 162.68, 160.40, 158.82, 152.49, 151.49, 148.40, 148.01, 147.41, 146.61, 138.37, 137.09, 135.29, 134.33, 132.32, 131.65, 131.28, 130.88, 123.48, 116.74, 109.78, 109.26, 108.36, 108.29, 107.17, 104.55, 101.43, 69.23, 60.74, 56.23, 52.89, 43.57, 41.72, 38.71, 17.14. ESI-MS m/z: 674.71[M+H]⁺

Example 20 Synthesis and Purification of 4β-NH-(1-aminoanthraquinone)-4'-demethylepipodophyllotoxin Compound (20)

(1) Synthesis of 4β-NH-(1-aminoanthraquinone)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 223 mg of 1-aminoanthraquinone were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(1-aminoanthraquinone)-4'-demethylepipodophyllotoxin.

(3) Separation and purification of 4β-NH-(1-aminoanthraquinone)-4'-demethylepipodophyllotoxin:

Separation and purification were performed using silica gel column chromatography and preparative column chromatography, respectively, in the same manner as in Example 1.

Compound (20) 4β-NH-(1-aminoanthraquinone)-4'-demethylepipodophyllotoxin, $C_{35}H_{27}NO_9$, red powder:

$^1$H NMR (300 MHz, CDCl₃): δ 10.04 (d, J=7.47 Hz, 1H), 8.24 (m, 2H), 7.75 (m, 3H), 7.65 (d, J=7.91 Hz, 1H), 7.08 (d, J=8.40 Hz, 1H), 6.79 (s, 1H), 6.59 (s, 1H), 6.37 (s, 2H), 5.98 (d, J=6.94 Hz, 2H), 5.06 (m, 1H), 4.72 (d, J=4.51 Hz, 1H), 4.41 (t, J=7.77 Hz, 1H), 3.90 (d, J=10.06 Hz, 2H), 3.78 (s, 6H), 3.26 (dd, J=14.11 Hz, 1H), 3.19-3.11 (m, 1H). $^{13}$C NMR (75 MHz, CDCl₃): δ 185.63, 183.23, 174.06, 152.56, 150.52, 148.47, 147.62, 137.19, 135.80, 134.98, 134.93, 134.45, 134.13, 133.40, 132.73, 131.75, 129.19, 126.78, 126.69, 116.70, 116.44, 113.46, 109.96, 109.17, 108.23, 101.53, 68.20, 56.20, 51.18, 43.57, 41.87, 38.28. ESI-MS m/z: 606.59[M+H]⁺

Example 21 Synthesis and Purification of 4β-NH-(2-aminoanthraquinone)-4'-demethylepipodophyllotoxin Compound (21)

(1) Synthesis of 4β-NH-(2-aminoanthraquinone)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 223 mg of 2-aminoanthraquinone were dissolved in 10 mL of tetrahydrofuran, 1 g of BaCO₃ a catalyst and 0.5 mL of triethylamine as an acid-binding agent were added as, the mixture was stirred at 600 rpm for 2 h in a 0° C. ice bath, then stirred at 600 rpm for 14 h at 27° C. room temperature, and a chloroform:acetone=20:1 system was used as a developing solvent to monitor the end of the reaction.

(2) The catalyst BaCO₃ was removed by filtration, and the filtrate was spun-dry to obtain crude 4β-NH-(2-aminoanthraquinone)-4'-demethylepipodophyllotoxin.

(3) Separation and purification of 4β-NH-(2-aminoanthraquinone)-4'-demethylepipodophyllotoxin:

Separation and purification were performed using silica gel column chromatography and preparative column chromatography, respectively, in the same manner as in Example 1.

Compound (21) 4β-NH-(2-aminoanthraquinone)-4'-demethylepipodophyllotoxin, $C_{35}H_{27}NO_9$, red powder:

$^1$H NMR (300 MHz, CDCl₃): δ 8.30-8.17 (m, 3H), 7.82-7.73 (m, 2H), 7.39 (s, 1H), 6.93-6.91 (m, 1H), 6.75 (s, 1H), 6.50 (s, 1H), 6.32 (s, 2H), 5.96 (d, J=9.0 Hz, 2H), 5.48 (s, 1H), 4.97 (s, 1H), 4.87 (d, J=6.0 Hz, 1H), 4.58 (s, 1H), 4.45 (d, J=6.0 Hz, 1H), 3.93 (d, J=9.0 Hz, 1H), 3.80 (s, 6H), 3.11 (s, 2H). $^{13}$C NMR (75 MHz, CDCl₃): δ 184.05, 181.75, 174.52, 151.99, 148.82, 147.97, 146.74, 135.88, 134.56, 134.37, 134.17, 133.68, 132.49, 130.41, 129.20, 127.35, 127.26, 124.75, 110.31, 109.32, 108.01, 101.95, 68.66, 56.72, 52.31, 43.65, 42.16, 38.57. ESI-MS m/z: 606.59[M+H]⁺

Example 22 Synthesis and Purification of 4β-NH-(1,2-diaminoanthraquinone)-4'-demethylepipodophyllotoxin Compound (22)

(1) Synthesis of 4β-NH-(1,2-diaminoanthraquinone)-4'-demethylepipodophyllotoxin: 400 mg (1 mmol) of 4'-demethylepipodophyllotoxin and 166 mg (1 mmol) of KI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin, 238 mg of 1,2-diaminoanthraquinone were dissolved in 10 mL of acetone, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(1,2-diaminoanthraquinone)-4'-demethylepipodophyllotoxin.

(3) Separation and purification of 4β-NH-(1,2-diaminoanthraquinone)-4'-demethylepipodophyllotoxin:

Separation and purification were performed using silica gel column chromatography and preparative column chromatography, respectively, in the same manner as in Example 1.

Compound (22) 4β-NH-(1,2-diaminoanthraquinone)-4'-demethylepipodophyllotoxin, $C_{35}H_{28}N_2O_9$, purple powder:

$^1$H NMR (400 MHz, CDCl₃): δ 8.24 (d, J=6.89 Hz, 1H), 8.16 (d, J=6.57 Hz, 1H), 7.79 (d, J=8.21 Hz, 1H), 7.75-7.68 (m, 2H), 6.78-6.73 (m, 2H), 6.18 (d, J=7.72 Hz, 2H), 5.79 (s, 1H), 5.67 (s, 1H), 5.48 (s, 1H), 5.07 (m, 1H), 4.88 (m, 1H), 4.37 (t, J=7.79 Hz, 1H), 4.10 (m, 1H), 3.91 (dd, J=11.14 Hz, 1H), 3.71 (s, 6H), 3.15 (dd, J=14.05 Hz, 1H), 3.03-2.95 (m, 1H). $^{13}$C NMR (100 MHz, CDCl₃): δ 186.14, 182.18, 174.58, 148.15, 147.40, 146.42, 141.91, 140.21, 134.80, 134.03, 133.66, 133.35, 133.13, 132.20, 130.44, 128.91, 126.79, 126.61, 121.00, 113.54, 111.16, 109.63, 109.16, 107.70, 101.43, 68.58, 56.48, 52.03, 43.24, 42.02, 38.19. ESI-MS m/z: 621.61[M+H]⁺

Example 23 Synthesis and Purification of 4β-NH-(1,5-diaminoanthraquinone)-4'-demethylepipodophyllotoxin Compound (23)

(1) Synthesis of 4β-NH-(1,5-diaminoanthraquinone)-4'-demethylepipodophyllotoxin: 400 mg (1 mmol) of 4'-demethylepipodophyllotoxin and 166 mg (1 mmol) of KI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin, 238 mg of 1,5-diaminoanthraquinone were dissolved in 10 mL of chloroform, 1 g of BaCO₃ as a catalyst and 0.5 mL of pyridine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(1,5-diaminoanthraquinone)-4'-demethylepipodophyllotoxin.

(3) Separation and purification of 4β-NH-(1,5-diaminoanthraquinone)-4'-demethylepipodophyllotoxin:

Separation and purification were performed using silica gel column chromatography and preparative column chromatography, respectively, in the same manner as in Example 1.

Compound (23) 4β-NH-(1,5-diaminoanthraquinone)-4'-demethylepipodophyllotoxin, $C_{35}H_{28}N_2O_9$, red powder:

$^1$H NMR (400 MHz, CDCl₃): δ 9.99 (d, J=7.64 Hz, 1H), 7.68 (d, J=7.43 Hz, 1H), 7.60 (t, J=7.97 Hz, 1H), 7.51 (d, J=7.39 Hz, 1H), 7.42 (d, J=7.88 Hz, 1H), 6.98 (d, J=8.47 Hz, 1H), 6.90 (d, J=8.23 Hz, 1H), 6.76 (s, 1H), 6.55 (s, 1H), 6.36 (s, 2H), 5.96 (d, J=10.18 Hz, 2H), 5.44 (s, 1H), 5.00 (dd, J=7.45 Hz, 1H), 4.67 (d, J=4.65 Hz, 1H), 4.35 (t, J=7.89 Hz, 1H), 3.87 (t, J=10.39 Hz, 1H), 3.80 (s, 6H), 3.22 (dd, J=14.12 Hz, 1H), 3.15-3.06 (m, 1H). $^{13}$C NMR (100 MHz, CDCl₃): δ 186.00, 185.04, 174.28, 150.79, 150.38, 148.47, 147.62, 146.45, 136.50, 135.71, 135.49, 134.81, 134.11, 131.95, 130.53, 129.39, 122.22, 116.68, 116.10, 115.27, 113.67, 113.34, 110.01, 109.26, 108.00, 101.54, 68.33, 56.50, 51.23, 43.48, 42.06, 38.34. ESI-MS m/z: 619.17[M+H]⁻

Example 24 Synthesis and Purification of 4β-NH-(2,6-diaminoanthraquinone)-4'-demethylepipodophyllotoxin Compound (24)

(1) Synthesis of 4β-NH-(2,6-diaminoanthraquinone)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 238 mg of 2,6-diaminoanthraquinone were dissolved in 10 mL of ethanol, 1 g of BaCO₃ as a catalyst and 0.5 mL of pyridine w as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(2,6-diaminoanthraquinone)-4'-demethylepipodophyllotoxin.

(3) Separation and purification of 4β-NH-(2,6-diaminoanthraquinone)-4'-demethylepipodophyllotoxin:

Separation and purification were performed using silica gel column chromatography and preparative column chromatography, respectively, in the same manner as in Example 1.

Compound (24) 4β-NH-(2,6-diaminoanthraquinone)-4'-demethylepipodophyllotoxin, $C_{35}H_{28}N_2O_9$, yellow powder:
$^1$H NMR (400 MHz, CDCl$_3$): δ 8.16 (d, J=8.52 Hz, 1H), 8.11 (d, J=8.42 Hz, 1H), 7.43 (d, J=2.57 Hz, 1H), 7.39 (d, J=2.37 Hz, 1H), 6.90 (dd, J=8.40 Hz, 1H), 6.83 (dd, J=8.56 Hz, 1H), 6.76 (s, 1H), 6.54 (s, 1H), 6.32 (s, 2H), 5.97 (dd, J=9.34 Hz, 2H), 4.98 (dd, J=7.29 Hz, 1H), 4.62 (dd, J=10.07 Hz, 2H), 4.47 (dd, J=10.33 Hz, 1H), 4.30 (t, J=6.73 Hz, 1H), 3.91 (dd, J=15.72 Hz, 2H), 3.77 (s, 6H), 3.12 (m, 2H). $^{13}$C NMR (100 MHz9CDCl$_3$): δ 178.25, 177.52, 167.40, 147.94, 147.27, 146.85, 143.87, 143.05, 132.58, 131.60, 131.28, 129.89, 127.53, 127.34, 126.14, 125.17, 125.14, 124.34, 124.06, 120.02, 119.68, 113.48, 106.49, 105.32, 103.42, 96.94, 63.70, 51.51, 47.32, 38.85, 37.09, 33.66. ESI-MS m/z: 643.60[M+Na]$^+$ Example 25 Synthesis and Purification of 4β-NH-(2,4-quinazolinediamine)-4'-demethylepipodophyllotoxin Compound (25)

(1) Synthesis of 4β-NH-(2,4-quinazolinediamine)-4'-demethylepipodophyllotoxin: 400 mg (1 mmol) of 4'-demethylepipodophyllotoxin and 166 mg (1 mmol) of KI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 160 mg of 2,4-quinazolinediamine were dissolved in 10 mL of acetonitrile, 1 g of BaCO$_3$ as a catalyst and 0.5 mL of pyridine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO$_3$ was removed by filtration, and the filtrate was spun-dry to obtain crude 4β-NH-(2,4-quinazolinediamine)-4'-demethylepipodophyllotoxin.

(3) Separation and purification of 4β-NH-(2,4-quinazolinediamine)-4'-demethylepipodophyllotoxin:

Separation and purification were performed using silica gel column chromatography and preparative column chromatography, respectively, in the same manner as in Example 1.

Compound (25) 4β-NH-(2,4-quinazolinediamine)-4'-demethylepipodophyllotoxin, $C_{29}H_{26}N_4O_7$, white powder:
$^1$H NMR (400 MHz, CDCl$_3$): δ 7.60 (m, 1H), 7.52 (d, J=6.31 Hz, 1H), 7.44 (d, J=6.95 1H), 7.15 (m, 1H), 6.82 (s, 1H), 6.40 (s, 1H), 6.31 (s, 2H), 5.88 (s, 1H), 5.78 (s, 1H), 5.60 (s, 1H), 5.41 (s, 1H), 4.54 (s, 1H), 4.45 (s, 1H), 3.94-3.90 (m, 1H), 3.73 (s, 6H), 3.07 (m, 2H). $^{13}$C NMR (100 MHz, CDCl$_3$): δ 175.17, 161.81, 158.44, 151.79, 1487.96, 147.21, 146.41, 133.89, 133.59, 132.21, 130.75, 130.09, 122.03, 121.94, 109.73, 109.32, 107.89, 101.42, 69.95, 56.39, 49.85, 43.61, 42.04, 38.16. ESI-MS m/z: 543.53[M+H]$^+$ Example 26 Synthesis and Purification of 4β-NH-(6-aminoquinoline)-4'-demethylepipodophyllotoxin Compound (26)

(1) Synthesis of 4β-NH-(6-aminoquinoline)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 144 mg of 6-aminoquinoline were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO$_3$ was removed by filtration, and the filtrate was spun-dry to obtain crude 4β-NH-(6-aminoquinoline)-4'-demethylepipodophyllotoxin.

(3) Separation and purification of 4β-NH-(6-aminoquinoline)-4'-demethylepipodophyllotoxin:

Separation and purification were performed using silica gel column chromatography and preparative column chromatography, respectively, in the same manner as in Example 1.

Compound (26) 4β-NH-(6-aminoquinoline)-4'-demethylepipodophyllotoxin, $C_{30}H_{26}N_2O_7$, light yellow powder:
$^1$H NMR (400 MHz, CDCl$_3$): δ 8.64 (d, J=3.26 Hz, 1H), 7.91 (t, J=8.44 Hz, 2H), 7.30 (dd, J=8.28 Hz, 1H), 7.06 (dd, J=9.02 Hz, 1H), 6.79 (s, 1H), 6.65 (d, J=2.43 Hz, 1H), 6.54 (s, 1H), 6.33 (s, 2H), 5.96 (d, J=6.47 Hz, 2H), 4.83 (m, 1H), 4.62 (d, J=4.74 Hz, 1H), 4.44 (m, 1H), 4.28 (d, J=5.96 Hz, 1H), 3.99 (m, 1H), 3.74 (s, 6H), 3.18 (dd, J=14.04 Hz, 1H), 3.13-3.04 (m, 1H). $^{13}$C NMR (100 MHz, CDCl$_3$): δ 174.50, 152.53, 148.39, 147.41, 146.59, 145.30, 143.31, 137.31, 134.96, 133.85, 131.82, 130.80, 130.00, 121.78, 120.86, 117.90, 109.91, 109.12, 108.30, 102.57, 101.58, 68.81, 56.26, 52.60, 43.55, 42.01, 38.62. ESI-MS m/z: 549.18[M+Na]$^+$ Example 27 Synthesis and Purification of 4β-NH-(5-aminoquinoline)-4'-demethylepipodophyllotoxin Compound (27)

(1) Synthesis of 4β-NH-(5-aminoquinoline)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 144 mg of 5-aminoquinoline were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO$_3$ was removed by filtration, and the filtrate was spun-dry to obtain crude 4β-NH-(5-aminoquinoline)-4'-demethylepipodophyllotoxin.

(3) Separation and purification of 4β-NH-(5-aminoquinoline)-4'-demethylepipodophyllotoxin:

Separation and purification were performed using silica gel column chromatography and preparative column chromatography, respectively, in the same manner as in Example 1.

Compound (27) 4β-NH-(5-aminoquinoline)-4'-demethylepipodophyllotoxin, $C_{30}H_{26}N_2O_7$, light yellow powder:

¹H NMR (400 MHz, CDCl₃): δ 8.89 (m, 1H), 8.36 (d, J=8.45 Hz, 1H), 7.58-7.52 (m, 2H), 7.44 (dd, J=8.55 Hz, 1H), 6.75 (s, 1H), 6.65 (d, J=7.53 Hz, 1H), 6.57 (s, 1H), 6.34 (s, 2H), 5.97 (d, J=4.83 Hz, 2H), 4.94 (t, J=4.56 Hz, 1H), 4.81 (d, J=4.57 Hz, 1H), 4.65 (d, J=4.93 Hz, 1H), 4.43 (m, 1H), 3.89 (m, 1H), 3.79 (s, 6H), 3.28 (dd, J=14.03 Hz, 1H), 3.15~3.06 (m, 1H). ¹³C NMR (100 MHz, CDCl₃): δ 174.47, 148.59, 147.81, 146.49, 143.05, 134.18, 132.42, 130.32, 131.85, 129.67, 119.42, 118.25, 110.13, 109.02, 107.92, 104.66, 103.95, 101.68, 68.73, 56.50, 52.70, 43.43, 42.22, 38.40. ESI-MS m/z: 527.19[M+H]⁺

Example 28 Synthesis and Purification of 4β-NH-(5-aminoisoquinoline)-4'-demethylepipodophyllotoxin Compound (28)

(1) Synthesis of 4β-NH-(5-aminoisoquinoline)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 144 mg of 5-aminoisoquinoline were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(5-aminoisoquinoline)-4'-demethylepipodophyllotoxin.

(3) Separation and purification of 4β-NH-(5-aminoisoquinoline)-4'-demethylepipodophyllotoxin:

Separation and purification were performed using silica gel column chromatography and preparative column chromatography, respectively, in the same manner as in Example 1.

Compound (28) 4β-NH-(5-aminoisoquinoline)-4'-demethylepipodophyllotoxin, C₃₀H₂₆N₂O₇, light yellow powder:

¹H NMR (400 MHz, CDCl₃): δ 9.16 (s, 1H), 8.45 (d, J=8.0 Hz, 1H), 7.53-7.46 (m, 2H), 7.40 (d, J=8 Hz, 1H), 6.74 (s, 1H), 6.70 (d, J=4 Hz, 1H), 6.56 (s, 1H), 6.50 (s, 1H), 6.35 (s, 2H), 5.96 (t, 2H), 4.90 (t, 1H), 4.64 (t, 2H), 4.41 (t, 1H), 3.94-3.87 (m, 1H), 3.76 (m, 6H), 3.25 (dd, J=12.0 Hz, 1H), 3.14-3.09 (m, 1H). ¹³C NMR (100 MHz, CDCl₃): δ 174.56, 152.93, 148.55, 147.81, 146.50, 142.39, 141.71, 134.18, 132.34, 130.40, 129.92, 127.79, 125.49, 117.54, 113.17, 110.10, 109.03, 107.95, 106.91, 101.65, 68.81, 56.50, 52.59, 43.43, 42.21, 38.53. ESI-MS m/z: 559.53[M+K]⁺

Example 29 Synthesis and Purification of 4β-NH-(8-aminoquinoline)-4'-demethylepipodophyllotoxin Compound (29)

(1) Synthesis of 4β-NH-(8-aminoquinoline)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 144 mg of 8-aminoquinoline were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(8-aminoquinoline)-4'-demethylepipodophyllotoxin.

(3) Separation and purification of 4β-NH-(8-aminoquinoline)-4'-demethylepipodophyllotoxin:

Separation and purification were performed using silica gel column chromatography and preparative column chromatography, respectively, in the same manner as in Example 1.

Compound (29) 4β-NH-(8-aminoquinoline)-4'-demethylepipodophyllotoxin, C₃₀H₂₆N₂O₇, light yellow powder:

¹H NMR (400 MHz, CDCl₃): δ 8.67 (d, J=3.16 Hz, 1H), 8.08 (d, J=8.06 Hz, 1H), 7.40-7.36 (m, 2H), 7.14 (d, J=8.16 Hz, 1H), 6.77 (s, 1H), 6.60 (d, J=7.59 Hz, 1H), 6.54 (s, 1H), 6.46 (d, J=6.68 Hz, 1H), 6.38 (s, 2H), 5.91 (dt, J=8.36 Hz, 2H), 5.69 (s, 1H), 4.86 (dd, J=5.98 Hz, 1H), 4.63 (d, J=4.87 Hz, 1H), 4.43 (t, J=7.95 Hz, 1H), 3.96 (m, 1H), 3.78 (s, 6H), 3.27 (dd, J=14.05 Hz, 1H), 3.15~3.06 (m, 1H). ¹³C NMR (100 MHz, CDCl₃): δ 174.88, 148.19, 147.50, 147.2, 146.47, 144.05, 137.65, 137.20, 134.08, 132.02, 130.79, 130.46, 128.76, 127.45, 121.82, 115.30, 109.67, 109.47, 108.04, 104.11, 101.43, 68.96, 56.48, 52.19, 43.48, 42.16, 38.90. ESI-MS m/z: 549.53[M+Na]⁺

Example 30 Synthesis and Purification of 4β-NH-(8-aminoquinaldine)-4'-demethylepipodophyllotoxin Compound (30)

(1) Synthesis of 4β-NH-(8-aminoquinaldine)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 158 mg of 8-aminoquinaldine were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(8-aminoquinaldine)-4'-demethylepipodophyllotoxin.

(3) Separation and purification of 4β-NH-(8-aminoquinaldine)-4'-demethylepipodophyllotoxin:

Separation and purification were performed using silica gel column chromatography and preparative column chromatography, respectively, in the same manner as in Example 1.

Compound (30) 4β-NH-(8-aminoquinaldine)-4'-demethylepipodophyllotoxin, C₃₁H₂₈N₂O₇, white powder:

¹H NMR (400 MHz, CDCl₃): δ 7.97 (d, J=8.38 Hz, 1H), 7.34 (t, J=7.88 Hz, 1H), 7.29 (d, J=8.40 Hz, 1H), 7.13 (d, J=7.77 Hz, 1H), 6.56 (m, 2H), 6.50 (d, J=5.95 Hz, 1H), 6.38 (s, 2H), 5.96 (s, 2H), 4.87 (dd, J=6.42 Hz, 1H), 4.68 (d, J=4.96 Hz, 1H), 4.42 (t, J=8.02 Hz, 1H), 3.96 (m, 1H), 3.84 (s, 1H), 3.78 (s, 6H), 3.33 (dd, J=14.08 Hz, 1H), 3.16-3.07 (m, 1H), 2.64 (s, 3H). ¹³C NMR (100 MHz, CDCl₃): δ

174.87, 156.30, 152.57, 148.11, 146.40, 143.52, 137.10, 136.16, 136.17, 135.34, 132.05, 130.68, 126.71, 126.28, 122.64, 115.19, 109.83, 109.64, 108.37, 104.12, 101.46, 69.02, 56.29, 52.16, 43.73, 42.16, 39.02, 25.17. ESI-MS m/z: 539.18[M+H]⁻

Example 31 Synthesis and Purification of 4β-NH-(5-indazolamine)-4'-demethylepipodophyllotoxin Compound (31)

(1) Synthesis of 4β-NH-(5-indazolamine)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 133 mg of 5-indazolamine were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(5-indazolamine)-4'-demethylepipodophyllotoxin.

(3) Separation and purification of 4β-NH-(5-indazolamine)-4'-demethylepipodophyllotoxin:

Separation and purification were performed using silica gel column chromatography and preparative column chromatography, respectively, in the same manner as in Example 1.

Compound (31) 4β-NH-(5-indazolamine)-4'-demethylepipodophyllotoxin, $C_{28}H_{35}N_3O_7$, white powder:

¹H NMR (400 MHz, CDCl₃): δ 7.9 (s, 1H), 7.33 (d, J=8.84 Hz, 1H), 7.75 (m, 2H), 6.69 (d, J=1.65 Hz, 1H), 6.51 (s, 1H), 6.69 (d, J=4 Hz, 1H), 6.51 (s, 1H), 6.34 (s, 2H), 5.94 (dd, J=6.0 Hz, 2H), 4.68 (t, J=4.44 Hz, 1H), 4.58 (d, J=4.92 Hz, 1H), 4.41 (t, J=7.94 Hz, 1H), 4.03-3.90 (m, 1H), 3.87 (d, J=5.26 Hz, 1H), 3.76 (s, 6H), 3.20 (dd, J=13.99 Hz, 1H), 3.07-2.99 (m, 1H). ¹³C NMR (100 MHz, CDCl₃): 175.10, 148.16, 147.57, 146.51, 142.39, 135.34, 134.13, 133.32, 131.86, 130.81, 130.67, 123.91, 118.14, 111.27, 109.89, 109.08, 108.01, 101.50, 98.06, 69.10, 56.49, 53.38, 43.40, 42.07, 38.69. ESI-MS m/z: 516.51[M+H]⁺

Example 32 Synthesis and Purification of 4β-NH-(6-indazolamine)-4'-demethylepipodophyllotoxin Compound (32)

(1) Synthesis of 4β-NH-(6-indazolamine)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain the I-4'-demethylepipodophyllotoxin; 510 mg of I-4'-demethylepipodophyllotoxin and 133 mg of 6-indazolamine were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(6-indazolamine)-4'-demethylepipodophyllotoxin.

(3) Separation and purification of 4β-NH-(6-indazolamine)-4'-demethylepipodophyllotoxin:

Separation and purification were performed using silica gel column chromatography and preparative column chromatography, respectively, in the same manner as in Example 1.

Compound (32) 4β-NH-(6-indazolamine)-4'-demethylepipodophyllotoxin, $C_{28}H_{35}N_3O_7$, white powder:

¹H NMR (400 MHz, CDCl₃): δ 7.98 (s, 1H), 7.31 (d, J=8.80 Hz, 1H), 7.68 (m, 2H), 6.62 (d, J=4.65 Hz, 1H), 6.50 (s, 1H), 6.49 (d, J=4 Hz, 1H), 6.41 (s, 1H), 6.32 (s, 2H), 5.91 (dd, J=4.30 Hz, 2H), 4.61 (t, J=4.44 Hz, 1H), 4.50 (d, J=4.92 Hz, 1H), 4.42 (t, J=3.94 Hz, 1H), 4.00 (m, 1H), 3.85 (d, J=4.26 Hz, 1H), 3.79 (s, 6H), 3.25 (dd, J=11.99 Hz, 1H), 3.05-2.99 (m, 1H). ¹³C NMR (100 MHz, CDCl₃): 175.20, 148.06, 147.54, 146.44, 142.32, 135.14, 134.03, 133.22, 131.80, 130.71, 130.59, 123.82, 118.10, 111.27, 109.99, 109.02, 108.00, 101.47, 98.08, 69.13, 56.45, 53.42, 43.45, 42.17, 38.73. ESI-MS m/z: 516.55, [M+H]⁺.

Example 33 Synthesis and Purification of 4β-NH-(7-indazolamine)-4'-demethylepipodophyllotoxin Compound (33)

(1) Synthesis of 4β-NH-(7-indazolamine)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 133 mg of 7-indazolamine were dissolved in 10 mL of tetrahydrofuran, 1 g of BaCO₃ as a catalyst and 0.5 mL of triethylamine as an acid-binding agent were added, the mixture was stirred at 600 rpm for 2 h in a 0° C. ice bath, then stirred at 600 rpm for 14 h at 27 room temperature, and a chloroform:acetone=20:1 system was used as a developing agent to monitor the reaction endpoint.

(2) The catalyst BaCO₃ was removed by filtration, and the filtrate was spun-dry to obtain crude 4β-NH-(7-indazolamine)-4'-demethylepipodophyllotoxin.

(3) Separation and purification of 4β-NH-(7-indazolamine)-4'-demethylepipodophyllotoxin:

Separation and purification were performed using silica gel column chromatography and preparative column chromatography, respectively, in the same manner as in Example 1.

Compound (33) 4β-NH-(7-indazolamine)-4'-demethylepipodophyllotoxin, $C_{28}H_{35}N_3O_7$, white powder:

¹H NMR (400 MHz, CDCl₃): δ 7.89 (s, 1H), 7.28 (d, J=3.84 Hz, 1H), 6.69 (d, J=4 Hz, 1H), 7.68 (m, 2H), 6.61 (d, J=3.95 Hz, 1H), 6.55 (s, 1H), 6.51 (s, 1H), 6.30 (s, 2H), 5.91 (dd, J=4.5 Hz, 2H), 4.62 (t, J=4.10 Hz, 1H), 4.59 (d, J=4.22 Hz, 1H), 4.40 (t, J=7.94 Hz, 1H), 4.00 (m, 1H), 3.87 (d, J=4.96 Hz, 1H), 3.71 (s, 6H), 3.21 (dd, J=11.99 Hz, 1H), 3.04-2.97 (m, 1H). ¹³C NMR (100 MHz, CDCl₃): 175.18, 148.10, 147.51, 146.50, 142.32, 135.31, 134.03, 133.30, 131.79, 130.71, 130.64, 123.85, 118.19, 111.20, 109.84, 109.00, 108.05, 101.45, 98.01, 69.18, 56.44, 53.32, 43.45, 42.05, 38.73. ESI-MS m/z: 516.57, [M+H]⁺.

Example 34 Synthesis and Purification of 4β-NH-(5-aminoindole)-4'-demethylepipodophyllotoxin Compound (34)

(1) Synthesis of 4β-NH-(5-aminoindole)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 132 mg of 5-aminoindole were dissolved in 10 mL of tetrahydrofuran, 1 g of $BaCO_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst $BaCO_3$ was removed by filtration, and the filtrate was spun-dry to obtain crude 4β-NH-(5-aminoindole)-4'-demethylepipodophyllotoxin.

(3) Separation and purification of 4β-NH-(5-aminoindole)-4'-demethylepipodophyllotoxin:

Separation and purification were performed using silica gel column chromatography and preparative column chromatography, respectively, in the same manner as in Example 1.

Compound (34) 4β-NH-(5-aminoindole)-4'-demethylepipodophyllotoxin, $C_{29}H_{26}N_2O_7$, black powder:

$^1H$ NMR (400 MHz, $CDCl_3$): δ 8.34 (s, 1H), 7.42 (d, J=8.06 Hz, 1H), 7.05 (m, 1H), 6.74 (s, 1H), 6.50 (s, 1H), 6.41 (m, 2H), 6.33 (s, 2H), 5.95 (dd, J=4.2 Hz, 2H), 5.50 (s, 1H), 4.61 (d, J=4.03 Hz, 1H), 4.54 (d, J=4.20 Hz, 1H), 4.30 (t, 1H), 4.11-3.95 (m, 1H), 3.81 (s, 1H), 3.79 (s, 6H), 3.18 (dd, J=12.05 Hz, 1H), 3.05-2.90 (m, 1H). $^{13}C$ NMR (100 MHz, $CDCl_3$): δ 174.15, 148.10, 147.42, 146.40, 139.96, 137.21, 134.16, 131.72, 131.23, 130.92, 122.33, 121.52, 120.82, 109.76, 109.14, 108.12, 102.45, 101.45, 92.65, 69.22, 56.49, 53.35, 43.45, 42.06, 38.75. ESI-MS m/z: 515.53, $[M+H]^+$.

Example 35 Synthesis and Purification of 4β-NH-(6-aminoindole)-4'-demethylepipodophyllotoxin Compound (35)

(1) Synthesis of 4β-NH-(6-aminoindole)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 132 mg of 6-aminoindole were dissolved in 10 mL of tetrahydrofuran, 1 g of $BaCO_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst $BaCO_3$ was removed by filtration, and the filtrate was spun-dry to obtain crude 4β-NH-(6-aminoindole)-4'-demethylepipodophyllotoxin.

(3) Separation and purification of 4β-NH-(6-aminoindole)-4'-demethylepipodophyllotoxin:

Separation and purification were performed using silica gel column chromatography and preparative column chromatography, respectively, in the same manner as in Example 1.

Compound (35) 4β-NH-(6-aminoindole)-4'-demethylepipodophyllotoxin, $C_{29}H_{26}N_2O_7$, black powder:

$^1H$ NMR (400 MHz, $CDCl_3$): δ 8.19 (s, 1H), 7.42 (d, J=8.36 Hz, 1H), 7.01 (m, 1H), 6.77 (s, 1H), 6.5 (s, 1H), 6.45 (m, 3H), 6.35 (s, 2H), 5.93 (dd, J=6.0 Hz, 2H), 5.53 (s, 1H), 4.65 (d, J=3.73 Hz, 1H), 4.57 (d, J=4.91 Hz, 1H), 4.34 (t, 1H), 4.06-3.95 (m, 1H), 3.79 (s, 1H), 3.77 (s, 6H), 3.18 (dd, J=14.0 Hz, 1H), 3.03-2.94 (m, 1H). $^{13}C$ NMR (100 MHz, $CDCl_3$): δ 175.25, 148.08, 147.48, 146.44, 149.94, 137.1, 134.06, 131.69, 131.11, 130.88, 122.29, 121.62, 120.89, 109.80, 109.17, 108.07, 102.41, 101.45, 92.75, 69.26, 56.50, 53.32, 43.42, 42.01, 38.82. ESI-MS m/z: $515.52[M+H]^+$

Example 36 Synthesis and Purification of 4β-NH-(7-aminoindole)-4'-demethylepipodophyllotoxin Compound (36)

(1) Synthesis of 4β-NH-(7-aminoindole)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 132 mg of 7-aminoindole were dissolved in 10 mL of tetrahydrofuran, 1 g of $BaCO_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst $BaCO_3$ was removed by filtration, and the filtrate was spun-dry to obtain crude 4β-NH-(7-aminoindole)-4'-demethylepipodophyllotoxin.

(3) Separation and purification of 4β-NH-(7-aminoindole)-4'-demethylepipodophyllotoxin:

Separation and purification were performed using silica gel column chromatography and preparative column chromatography, respectively, in the same manner as in Example 1.

Compound (36) 4β-NH-(7-aminoindole)-4'-demethylepipodophyllotoxin, $C_{29}H_{26}N_2O_7$, black powder:

$^1H$ NMR (400 MHz, $CDCl_3$): δ 8.15 (s, 1H), 7.40 (d, J=8.32 Hz, 1H), 7.00 (m, 1H), 6.74 (s, 1H), 6.46 (s, 1H), 6.40 (m, 2H), 6.32 (s, 2H), 5.91 (dd, J=4.0 Hz, 2H), 5.50 (s, 1H), 4.62 (d, J=4.13 Hz, 1H), 4.51 (d, J=4.87 Hz, 1H), 4.32 (t, 1H), 4.08-3.96 (m, 1H), 3.80 (s, 1H), 3.78 (s, 6H), 3.16 (d, J=12.0 Hz, 1H), 3.05-2.97 (m, 1H). $^{13}C$ NMR (100 MHz, $CDCl_3$): δ 175.15, 148.02, 147.44, 146.35, 139.94, 137.12, 134.26, 131.79, 131.20, 130.78, 122.22, 121.60, 120.84, 109.76, 109.17, 108.02, 102.46, 101.40, 92.57, 69.36, 56.52, 53.36, 43.45, 42.04, 38.72. ESI-MS m/z: 515.56, [M+H]$^+$.

Example 37 Synthesis and Purification of 4β-NH-(2-(2-aminophenyl) benzimidazole)-4'-demethylepipodophyllotoxin COMPOUND (37)

(1) Synthesis of 4β-NH-(2-(2-aminophenyl) benzimidazole)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 209 mg of 2-(2-aminophenyl) benzimidazole were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO$_3$ was removed by filtration, and the filtrate was spun-dry to obtain crude 4β-NH-(2-(2-aminophenyl) benzimidazole)-4'-demethylepipodophyllotoxin.

(3) Separation and purification of 4β-NH-(2-(2-aminophenyl) benzimidazole)-4'-demethylepipodophyllotoxin:

Separation and purification were performed using silica gel column chromatography and preparative column chromatography, respectively, in the same manner as in Example 1.

Compound (37) 4β-NH-(2-(2-aminophenyl) benzimidazole)-4'-demethylepipodophyllotoxin, C$_{34}$H$_{29}$N$_3$O$_7$, white powder:

$^1$H NMR (400 MHz, CDCl$_3$): δ 10.12 (d, J=4 Hz, 1H), 9.39 (d, J=4 Hz, 1H), 7.64 (d, J=4 Hz, 1H), 7.53 (d, J=8 Hz, 1H), 7.32 (m, 2H), 7.17 (m, 1H), 6.77 (d, J=12.0 Hz, 2H), 6.73-6.69 (m, 1H), 6.51 (s, 1H), 6.38 (s, 2H), 5.89 (s, 2H), 5.58 (s, 1H), 4.94 (dd, J=8 Hz, 1H), 4.66 (d, J=4 Hz, 1H), 4.35 (t, 1H), 3.97-3.92 (m, 1H), 3.76 (s, 6H), 3.33 (dd, J=16.0 Hz, 1H), 3.12~3.01 (m, 1H). $^{13}$C NMR (100 MHz, CDCl$_3$): δ 175.21, 151.67, 147.98, 147.31, 147.25, 146.43, 142.90, 134.00, 132.79, 131.56, 131.30, 131.05, 130.54, 127.41, 123.23, 122.12, 119.08, 116.20, 111.27, 110.72, 110.41, 109.64, 109.51, 108.07, 101.33, 68.98, 56.47, 51.49, 43.54, 42.31, 38.88. ESI-MS m/z: 592.60[M+H]$^+$

Example 38 Synthesis and Purification of 4β-NH-(2-(5-amino-2-methylphenyl)-4-(3-pyridyl) pyrimidine)-4'-demethylepipodophyllotoxin COMPOUND (38)

(1) Synthesis of 4β-NH-(2-(5-amino-2-methylphenyl)-4-(3-pyridyl) pyrimidine)-4'-demethylepipodophyllotoxin: 400 mg (1 mmol) of 4'-demethylepipodophyllotoxin and 149 mg (1 mmol) of NaI were dried for 1 h, then dissolved in 10 mL of acetonitrile, 0.45 mL of boron trifluoride diethyl ether was dropwise added in a 0° C. ice bath, the mixture was stirred at 600 rpm for 1 h at room temperature, and then spun-dry to obtain I-4'-demethylepipodophyllotoxin; 510 mg of I-4'-demethylepipodophyllotoxin and 277 mg of 2-(5-amino-2-methylphenyl)-4-(3-pyridyl) pyrimidine were dissolved in 10 mL of tetrahydrofuran, 1 g of BaCO$_3$ as a catalyst and 0.5 mL of triethylamine as an acid-binding agent were added, the mixture was stirred at 600 rpm for 2 h in a 0° C. ice bath, then stirred at 600 rpm for 14 h at 27° C. room temperature, and a chloroform:acetone=20:1 system was used as a developing agent to monitor the reaction endpoint.

(2) The catalyst BaCO$_3$ was removed by filtration, and the filtrate was spun-dry to obtain crude 4β-NH-(2-(5-amino-2-methylphenyl)-4-(3-pyridine) pyrimidine)-4'-demethylepipodophyllotoxin.

(3) Separation and purification of 4β-NH-(2-(5-amino-2-methylphenyl)-4-(3-pyridyl) pyrimidine)-4'-demethylepipodophyllotoxin:

Separation and purification were performed using silica gel column chromatography and preparative column chromatography, respectively, in the same manner as in Example 1.

Compound (38) 4β-NH-(2-(5-amino-2-methylphenyl)-4-(3-pyridyl) pyrimidine)-4'-demethylepipodophyllotoxin, C$_{37}$H$_{33}$N$_5$O$_7$, white powder:

$^1$H NMR (400 MHz, CDCl$_3$): δ 9.22 (s, 1H), 8.63 (d, J=4.78 Hz, 1H), 8.42 (d, J=5.16 Hz, 1H), 8.28 (d, J=8.01 Hz, 1H), 7.65 (d, J=2.04 Hz, 1H), 7.34 (dd, J=7.96 Hz, 1H), 7.15 (s, 1H), 7.10 (d, J=5.21 Hz, 1H), 7.03 (d, J=8.15 Hz, 1H), 6.78 (s, 1H), 6.47 (s, 1H), 6.32 (s, 2H), 6.24 (dd, J=9.37 Hz, 1H), 5.88 (d, J=15.25 Hz, 2H), 4.68 (t, J=4.68 Hz, 1H), 4.52 (d, J=4.85 Hz, 1H), 4.32 (t, J=7.97 Hz, 1H), 4.08 (m, 1H), 4.00 (m, 1H), 3.75 (s, 6H), 3.06 (dd, J=13.99 Hz, 1H), 2.99-2.90 (m, 1H), 2.28 (s, 3H). $^{13}$C NMR (100 MHz, CDCl$_3$): δ 175.11 (C-12), 162.66, 160.41, 158.81, 151.36, 148.31, 147.99, 147.36, 146.59, 146.51, 138.33, 134.45, 134.13, 132.59, 131.86, 131.27, 130.88, 130.66, 123.65, 116.97, 109.79, 109.22, 108.32, 108.02, 107.29, 104.73, 101.41, 69.25, 56.44, 52.87, 43.39, 41.85, 38.71, 17.14. ESI-MS m/z: 660.68[M+H]$^+$

Test Example 1 Activity Test of the Compound of the Present Invention for Inhibiting Tumor Cells I. Test Materials Test compounds: Compounds prepared in Examples 1-30, numbered Compounds 1-30, respectively;

A control compound: etoposide;

A cell strain: Hepatoma HepG2, cervical cancer Hela, lung cancer A549, breast cancer MCF7 cell line and human normal liver cell HL7702 were purchased from Wuhan Boster Biological Technology Co., Ltd.;

II. Test Methods

HepG2, Hela, A549, MCF 7 cells in logarithmic growth phase and human normal hepatocytes HL7702 were centrifuged at 1500 rpm for 5 min, and the supernatant was discarded; the cells were digested with a suitable amount of trypsin, and then suspended with a suitable amount of culture medium (HepG2, Hela and HL7702 cells were suspended with penicillin-streptomycin RPMI1640 culture medium containing 10% calf serum, A549 and MCF 7 cells with penicillin-streptomycin high glucose DMEM culture medium containing 10% calf serum, to adjust the cell concentration to 1.5×10⁴ cells/well, the cells were seeded in 96-well plates, and the following experimental groups were set:

One blank negative control group; 30 test groups of the same concentration (i. e.: Compound 1-30 groups); 1 control group: etoposide.

0.10 mL of the cell suspension was added to each well, and incubated at 37° C., 5% $CO_2$ and saturated humidity for 12 h, and the culture medium was discarded when the cell density was nearly 70%. In each of the 30 test groups, 0.10 mL of a culture medium (penicillin-streptomycin RPMI1640 culture medium containing 10% calf serum for HepG2, Hela and HL7702 cells, penicillin-streptomycin high glucose DMEM culture medium containing 10% calf serum for A549 and MCF 7 cells) containing at least 6 concentration gradient compounds was added, and the concentrations of the compounds (1)-(30) groups were consistent; the dosage of etoposide group was the same as that of compounds (1)-(30); the negative control group was treated with the culture medium (penicillin-streptomycin RPMI1640 culture medium containing 10% calf serum for HepG2, Hela and HL7702 cells, penicillin-streptomycin high glucose DMEM culture medium containing 10% calf serum for A549 and MCF 7 cells) with a final concentration of 0.5% DMSO, and each group was treated with 3 duplicate wells and cultured for 48 h. 100 µl of 5 mg/ml MTT was added per well, standing for 4 h at 37° C. 100 µl of DMSO was added to each well, followed by shaking on a shaker for 10 min at 37° C., the absorbance (OD) was measured at 492 nm, and the MTT ratio was calculated as the OD value of drug group/OD value of negative control group.

III. Test Results

The results of the tests are shown in Table 1. As can be seen from Table 1, the antitumor activities of most of the compounds (1)-(30) on HepG2, Hela, A549 and MCF 7 cell lines are obviously improved compared with that of the podophylloid derivative etoposide which is currently marketed as an anticancer drug.

TABLE 1

$IC_{50}$ values of 4β-amino-substituted podophylloid derivatives against in vitro tumor strains and normal cell lines

| Compounds | $IC_{50}$ (µM) | | | | |
|---|---|---|---|---|---|
| | HepG2 | HeLa | A549 | MCF7 | HL7702 |
| 1 | 0.9 ± 0.05 | 0.7 ± 0.1 | 0.2 ± 0.01 | 0.7 ± 0.01 | >100 |
| 2 | 9.6 ± 0.8 | 2.5 ± 0.3 | 2.9 ± 0.4 | 2.9 ± 0.1 | >100 |
| 3 | 52.0 ± 8.4 | 24.58 ± 3.2 | >100 | 17.5 ± 2.1 | >100 |
| 4 | 4.7 ± 0.4 | 4.6 ± 0.2 | 2.2 ± 0.3 | 3.4 ± 0.6 | >100 |
| 5 | 9.1 ± 1.2 | 6.5 ± 0.5 | >100 | >100 | >100 |
| 6 | >100 | 19.2 ± 1.9 | 14.3 ± 2.3 | 24.5 ± 4.4 | 13.8 ± 1.9 |
| 7 | 0.8 ± 0.01 | 0.7 ± 0.03 | 0.3 ± 0.04 | 0.6 ± 0.03 | >100 |
| 8 | >100 | >100 | >100 | >100 | >100 |
| 9 | 4.1 ± 1.1 | 3.1 ± 0.2 | 2.3 ± 0.1 | 1.4 ± 0.3 | 16.3 ± 2.8 |
| 10 | 4.6 ± 0.4 | 2.7 ± 0.3 | 1.2 ± 0.2 | 1.0 ± 0.1 | 37.0 ± 4.8 |
| 11 | 1.6 ± 0.1 | 1.5 ± 0.1 | 3.0 ± 0.4 | 1.0 ± 0.2 | >100 |
| 12 | 0.3 ± 0.02 | 0.5 ± 0.01 | 0.2 ± 0.02 | 0.4 ± 0.03 | 50 ± 4.9 |
| 13 | 1.8 ± 0.2 | 2.1 ± 0.3 | 2.4 ± 0.2 | 1.3 ± 0.2 | 33.6 ± 1.5 |
| 14 | 0.9 ± 0.1 | 0.9 ± 0.01 | 0.5 ± 0.01 | 0.4 ± 0.01 | 43.3 ± 2.8 |
| 15 | 2.5 ± 0.6 | 3.8 ± 0.2 | 2.2 ± 0.9 | 4.8 ± 0.9 | 30.5 ± 2.7 |
| 16 | 0.6 ± 0.01 | 0.4 ± 0.01 | 0.2 ± 0.02 | 0.3 ± 0.01 | 140 ± 20.3 |
| 17 | 1.9 ± 0.2 | 0.8 ± 0.1 | 1.0 ± 0.1 | 0.8 ± 0.1 | 38.4 ± 2.6 |
| 18 | 3.6 ± 0.3 | 4.8 ± 0.2 | 2.8 ± 0.1 | 1.7 ± 0.2 | >100 |
| 19 | 6.6 ± 0.1 | 4.8 ± 0.4 | 7.7 ± 0.6 | 9.5 ± 0.8 | >100 |
| 20 | 8.8 ± 2.1 | 8.5 ± 2.1 | 1.8 ± 0.2 | 2.3 ± 0.1 | 53.7 ± 5.3 |
| 21 | 1.1 ± 0.4 | 1.9 ± 0.3 | >100 | 4.0 ± 0.5 | 55.4 ± 6.2 |
| 22 | >100 | >100 | >100 | 18.1 ± 2.8 | >100 |
| 23 | >100 | >100 | >100 | >100 | >100 |
| 24 | >100 | >100 | >100 | 4.2 ± 1.1 | >100 |
| 25 | 9.8 ± 1.7 | 3.6 ± 0.9 | 3.6 ± 0.8 | 6.1 ± 1.3 | 16.9 ± 2.5 |
| 26 | 10.0 ± 1.9 | 5.7 ± 1.1 | 2.0 ± 0.5 | 4.3 ± 0.8 | 22.8 ± 4.2 |
| 27 | 1.6 ± 0.8 | 2.1 ± 1.0 | 1.3 ± 0.2 | 2.4 ± 0.9 | 15.6 ± 1.8 |
| 28 | 2.8 ± 1.6 | 1.9 ± 0.9 | 1.4 ± 0.6 | 2.5 ± 0.9 | 19.8 ± 2.1 |
| 29 | 4.5 ± 1.5 | 3.8 ± 0.2 | 2.8 ± 0.4 | 1.5 ± 0.4 | 73.0 ± 7.8 |
| 30 | 5.0 ± 1.1 | 4.2 ± 0.8 | 0.5 ± 0.05 | 3.0 ± 0.5 | >100 |
| 31 | 6.8 ± 1.5 | 4.3 ± 0.9 | 1.7 ± 0.3 | 3.5 ± 0.3 | >100 |
| 32 | 19.4 ± 1.5 | 6.4 ± 1.8 | 25.6 ± 3.7 | 21.4 ± 5.9 | 17.7 ± 2.2 |
| 33 | 22.5 ± 2.6 | 34.0 ± 1.1 | 24.5 ± 5.0 | 16.4 ± 0.9 | 29.8 ± 1.9 |
| 34 | >100 | 21.7 ± 5.3 | >100 | 76.3 ± 5.7 | >100 |
| 35 | 19.5 ± 2.4 | 21.1 ± 2.9 | 6.5 ± 1.0 | 34.5 ± 3.8 | >100 |
| 36 | 15.4 ± 2.2 | 15.4 ± 6.1 | 19.5 ± 1.5 | 8.0 ± 5.5 | 31.5 ± 3.2 |
| 37 | >100 | 48.6 ± 6.2 | >100 | >100 | >100 |
| 38 | 29.5 ± 3.2 | 35.1 ± 5.9 | 15.5 ± 2.0 | 14.5 ± 3.8 | >100 |
| Etoposide | 20.0 ± 1.3 | 21.4 ± 1.6 | 22.5 ± 1.8 | 53.8 ± 5.6 | 24.6 ± 3.8 |

The invention claimed is:
1. A compound of formula (V) or a pharmaceutically acceptable salt thereof:
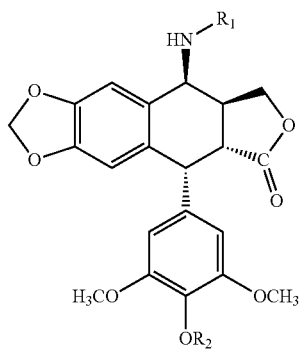
Formula (V)
wherein $R_1$ is selected from
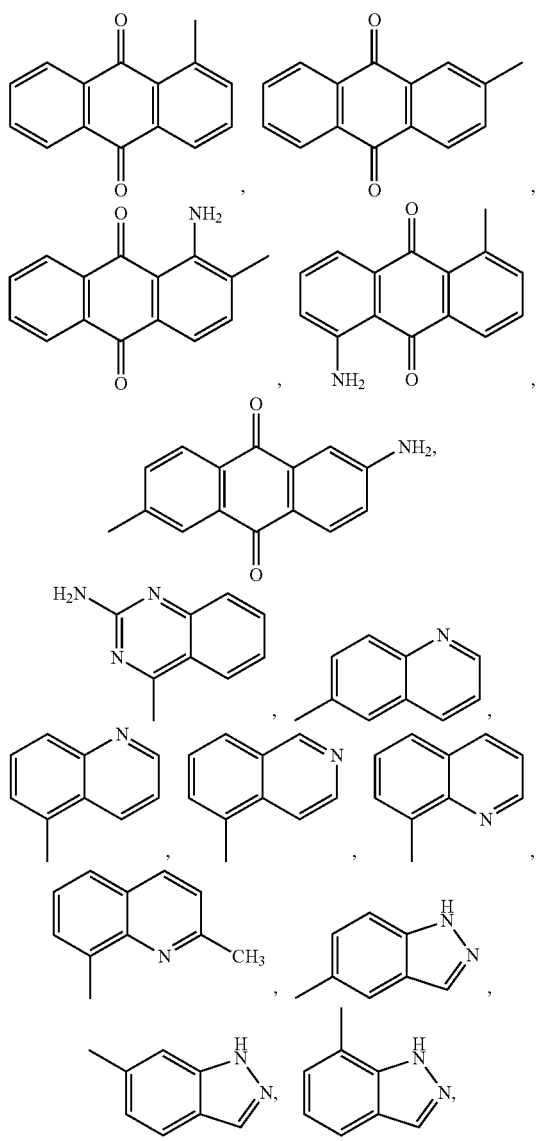
$R_2$ is hydrogen or —$CH_3$,
provided that when $R_2$ is hydrogen, $R_1$ is selected from
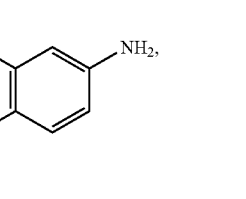
;

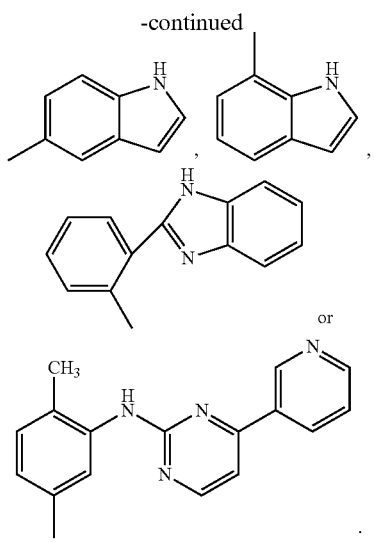

2. A method for preparing the compound of claim 1, the method comprising the steps of:
A. introducing iodine into position-4 of the C ring in podophyllotoxin or 4'-demethylepipodophyllotoxin through an iodine substitution reaction to form iodopodophyllotoxin or iodo4'-demethylepipodophyllotoxin; and
B. introducing a reaction monomer into position-4 of the C ring in iodopodophyllotoxin through a nucleophilic substitution reaction, wherein the reaction monomer is selected from the group consisting of 1-amino anthraquinone, 2-amino anthraquinone, 1,2-diamino anthraquinone, 1,5-diamino anthraquinone, 2,6-diamino anthraquinone, 2,4-quinazolinediamine, 6-aminoquinoline, 5-aminoquinoline, 5-aminoisoquinoline, 8-aminoquinoline, 8-aminoquinaldine, 5-indazolamine, 6-indazolamine, 7-indazolamine, 5-aminoindole, 6-aminoindole, 7-aminoindole, 2-(2-aminophenyl) benzimidazole and N-(5-amino-2-methylphenyl)-4-(3-pyridyl)-2-aminopyrimidine, or introducing a reaction monomer into position-4 of the C ring in iodo4'-demethylepipodophyllotoxin through a nucleophilic substitution reaction, wherein the reaction monomer is selected from the group consisting of 1-amino anthraquinone, 2-amino anthraquinone, 1,2-diamino anthraquinone, 1,5-diamino anthraquinone, 2,6-diamino anthraquinone, 2,4-quinazolinediamine, 6-aminoquinoline, 5-aminoquinoline, 5-aminoisoquinoline, 8-aminoquinoline, 8-aminoquinaldine, 5-indazolamine, 6-indazolamine, 7-indazolamine, 5-aminoindole, 7-aminoindole, 2-(2-aminophenyl) benzimidazole and N-(5-amino-2-methylphenyl)-4-(3-pyridyl)-2-aminopyrimidine.

3. The method of claim 2, wherein the iodine substitution reaction is performed under the following conditions: dissolving podophyllotoxin or 4'-demethylepipodophyllotoxin in acetonitrile, adding NaI or KI, and boron trichloride diethyl ether followed by stirring, wherein a molar ratio of podophyllotoxin or 4'-demethylepipodophyllotoxin to NaI or KI is 1:1-1.5.

4. The method of claim 3, wherein boron trichloride diethyl ether is added dropwise in an ice bath, followed by stirring for reaction at a certain temperature.

5. The method of claim 4, wherein the certain temperature is 15-40° C.

6. The method of claim 2, wherein the nucleophilic substitution reaction is performed under the following conditions: dissolving the reaction monomer with iodopodophyllotoxin or iodo4'-demethylepipodophyllotoxin in an organic solvent, adding a catalyst and an acid-binding agent, followed by stirring, wherein a molar ratio of the reaction monomer to iodopodophyllotoxin or iodo4'-demethylepipodophyllotoxin is 3:1-1:1; the organic solvent is tetrahydrofuran, acetone, chloroform, ethanol or acetonitrile; the catalyst is BaCO₃; and the acid-binding agent is triethylamine or pyridine.

7. The method of claim 6, wherein the nucleophilic substitution reaction is performed in an ice bath followed by performing reaction at a certain temperature.

8. The method of claim 7, wherein the certain temperature is 15-40° C.

9. The method of claim 2, further comprising the steps of: filtering the reaction solution after the nucleophilic substitution reaction, spin-drying the filtrate, and performing preparation and separation by using silica gel column chromatography or a reverse phase chromatography column to obtain purified 4β-amino substituted podophyllotoxin derivatives products.

10. A method of antitumor treatment by administering an effective amount of the compound or the salt thereof of claim 1.

11. An antitumor pharmaceutical composition comprising an effective amount of the compound or the salt thereof of claim 1 and a pharmaceutically acceptable carrier.

* * * * *